(12) United States Patent
Ji

(10) Patent No.: US 11,963,814 B2
(45) Date of Patent: Apr. 23, 2024

(54) SYSTEMS AND METHODS FOR DETERMING TARGET SCANNING PHASE

(71) Applicant: SHANGHAI UNITED IMAGING HEALTHCARE CO., LTD., Shanghai (CN)

(72) Inventor: Min Ji, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 364 days.

(21) Appl. No.: 17/349,959

(22) Filed: Jun. 17, 2021

(65) Prior Publication Data
US 2022/0287674 A1 Sep. 15, 2022

(30) Foreign Application Priority Data

Mar. 15, 2021 (CN) .......................... 202110274057.0

(51) Int. Cl.
A61B 6/02 (2006.01)
A61B 6/00 (2006.01)
A61B 6/50 (2024.01)
G06T 7/246 (2017.01)
G06T 7/73 (2017.01)

(52) U.S. Cl.
CPC .............. *A61B 6/541* (2013.01); *A61B 6/481* (2013.01); *A61B 6/503* (2013.01); *G06T 7/248* (2017.01); *G06T 7/73* (2017.01); *G06T 2200/04* (2013.01); *G06T 2207/10016* (2013.01); *G06T 2207/10081* (2013.01); *G06T 2207/20036* (2013.01); *G06T 2207/30048* (2013.01); *G06T 2207/30061* (2013.01)

(58) Field of Classification Search
None
See application file for complete search history.

(56) References Cited

U.S. PATENT DOCUMENTS

| 2009/0003513 | A1 | 1/2009 | Grass et al. |
| 2010/0040193 | A1 | 2/2010 | Lessick |
| 2019/0206051 | A1* | 7/2019 | Cao ...................... A61B 5/0037 |
| 2020/0219252 | A1* | 7/2020 | Tsuyuki ................. A61B 6/481 |

* cited by examiner

Primary Examiner — Hoon K Song
(74) Attorney, Agent, or Firm — METIS IP LLC

(57) ABSTRACT

Systems and methods for scanning a region of interest (ROI) of a subject are provided. The ROI may undergo a physiological motion. The systems may obtain a reference image of the ROI to be scanned by a target scan. The systems may determine a scanning region based on the reference image. The systems may obtain a plurality of images of the scanning region by performing a pre-scan on the scanning region. The systems may determine, based on the plurality of images of the scanning region, a target scanning phase of the ROI for performing the target scan.

20 Claims, 10 Drawing Sheets

1100

Obtaining morphological information of a ROI based on a 3D image of the ROI — 1101

Determining, based on the morphological information of the ROI, a scanning angle for a pre-scan — 1103

Performing the pre-scan on the scanning region at the scanning angle — 1105

800

| Determining a variation of projection values of each physical point in a scanning region over time based on an image sequence of the scanning region | 801 |

↓

| Determining a variation of projection values of each POI over time based on the variation of projection values of each physical point in a scanning region over time | 803 |

↓

| Determining a target scanning phase based on the variation of projection values of each POI over time and a physiological motion curve | 805 |

FIG. 8

SYSTEMS AND METHODS FOR DETERMING TARGET SCANNING PHASE

CROSS-REFERENCE TO RELATED APPLICATIONS

This application claims priority of Chinese Patent Application No. 202110274057.0, field on Mar. 15, 2021, the contents of which are hereby incorporated by reference.

TECHNICAL FIELD

The disclosure generally relates to the field of medical scanning, and more particularly relates to systems and methods for determining a target scanning phase of a region of interest (ROI) for scanning the ROI.

BACKGROUND

Medical imaging technologies have been widely used for clinical examination and medical diagnosis. In some occasions, an ROI to be scanned may undergo a physiological motion, which needs to be considered to improve the scanning accuracy (e.g., reduce motion artifacts in a resulting image). For example, cardiac imaging (e.g., a coronary artery scan using a computed tomography (CT) device) is often used to examine the coronary artery. The cardiac imaging needs to be performed on the heart of a patient when the heart is under a relatively static motion state. The key to a successful scan is to determine a target scanning phase, at which the ROI is in a relatively static motion state, for a target scan. Therefore, it is desirable to provide systems and methods for determining a target scanning phase of an ROI for performing a target scan.

SUMMARY

In some embodiments, a system is provided. The system may include at least one storage device including a set of instructions for scanning a region of interest (ROI) of a subject. The ROI may undergo a physiological motion. The system may also include at least one processor configured to communicate with the at least one storage device. When executing the set of instructions, the at least one processor may be configured to direct the system to perform following operations. The system may obtain a reference image of the ROI to be scanned by a target scan. The system may determine a scanning region based on the reference image. The system may also obtain a plurality of images of the scanning region by performing a pre-scan on the scanning region. The system may further determine, based on the plurality of images of the scanning region, a target scanning phase of the ROI for performing the target scan.

In some embodiments, the plurality of images may be sequentially acquired during the pre-scan with the subject being located at a fixed position relative to a radiation source of an imaging device.

In some embodiments, the determining, based on the plurality of images of the scanning region, a target scanning phase of the ROI may include obtaining physiological motion data indicating the physiological motion of the ROI during the pre-scan; for each of the plurality of images, determining a feature element from the image; and determining, based on the feature element of each image and the physiological motion data, the target scanning phase of the ROI.

In some embodiments, the determining, based on the feature element of each image and the physiological motion data, the target scanning phase of the ROI may include determining, based on the physiological motion data, an initial time interval during which the ROI is in a steady status; and determining, from the initial time interval, the target scanning phase of the ROI based on the feature element of each image.

In some embodiments, for each of the plurality of images, the determining a feature element from the image may include determining, based on at least one of the plurality of images, a target coordinate; and for each of the plurality of images, determining, from the image, an element having the target coordinate as the feature element of the image.

In some embodiments, the determining, from the initial time interval, the target scanning phase of the ROI based on the feature element of each image may include for each of the plurality of images, determining a projection value of the feature element of the image; determining a first variation of the projection values of the feature elements of the plurality of images over time; and determining, from the initial time interval, the target scanning phase based on the first variation.

In some embodiments, for each of the plurality of images, the determining a feature element from the image may include for each of the plurality of images, determining, based on the image, a target projection value; and determining, from the image, an element having the target projection value as the feature element of the image.

In some embodiments, the determining, based on the image, a target projection value corresponding to a feature point of the ROI may include determining a plurality of projection values of a plurality of elements in the image; determining, among the plurality of projection values, a maximum projection value; and determining the target projection value based on the maximum projection value.

In some embodiments, the determining, from the initial time interval, the target scanning phase of the ROI based on the feature element of each image may include for each of the plurality of images, determining a coordinate of the feature element of the image; determining a second variation of the coordinates of the feature elements of the plurality of images over time; and determining, from the initial time interval, the target scanning phase based on the second variation.

In some embodiments, the physiological motion data may include an electrocardiograph (ECG) curve.

In some embodiments, the ROI may include the heart of a subject, and the physiological motion may include a cardiac motion; or the ROI may include the lungs of a subject, and the physiological motion may include a respiratory motion.

In some embodiments, the subject may be injected with a contrast agent before the pre-scan.

In some embodiments, the scanning region may include multiple sub-regions. The determining, based on the plurality of images of the scanning region, a target scanning phase of the ROI for performing the target scan further may include determining, based on the plurality of images of the scanning region, a target scanning phase for each of the multiple sub-regions. The operations further include directing an imaging device to perform the target scan on the ROI according to the target scanning phases corresponding to the multiple sub-regions; and for each of the multiple target scanning phases, generating a target image of the ROI based on target scan data of the ROI acquired during a target time period corresponding to the target scanning phase.

In some embodiments, the performing the pre-scan on the scanning region may include obtaining morphological information of the ROI based on a 3D image of the ROI; determining, based on the morphological information of the ROI, a scanning angle for the pre-scan; and performing the pre-scan on the scanning region at the scanning angle.

In another aspect of the present disclosure, a method implemented by a computing device including at least one processor and at least one storage device is provided. The method may include obtaining a reference image of the ROI to be scanned by a target scan. The method may include determining a scanning region based on the reference image. The method may also include obtaining a plurality of images of the scanning region by performing a pre-scan on the scanning region. The method may further include determining, based on the plurality of images of the scanning region, a target scanning phase of the ROI for performing the target scan.

In some embodiments, the plurality of images may be sequentially acquired during the pre-scan with the subject being located at a fixed position relative to a radiation source of an imaging device.

In some embodiments, the determining, based on the plurality of images of the scanning region, a target scanning phase of the ROI may include obtaining physiological motion data indicating the physiological motion of the ROI during the pre-scan; for each of the plurality of images, determining a feature element from the image; and determining, based on the feature element of each image and the physiological motion data, the target scanning phase of the ROI.

In some embodiments, the determining, based on the feature element of each image and the physiological motion data, the target scanning phase of the ROI may include determining, based on the physiological motion data, an initial time interval during which the ROI is in a steady status; and determining, from the initial time interval, the target scanning phase of the ROI based on the feature element of each image.

In some embodiments, the physiological motion data may include an electrocardiograph (ECG) curve.

In another aspect of the present disclosure, a non-transitory computer readable medium is provided. The medium may include executable instructions that, when executed by at least one processor, direct the at least one processor to perform a method for scanning a region of interest (ROI) of a subject. The ROI may undergo a physiological motion. The method may include obtaining a reference image of the ROI to be scanned by a target scan. The method may include determining a scanning region based on the reference image. The method may also include obtaining a plurality of images of the scanning region by performing a pre-scan on the scanning region. The method may further include determining, based on the plurality of images of the scanning region, a target scanning phase of the ROI for performing the target scan.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 8 is a flowchart illustrating an exemplary process for determining a target scanning phase of an ROI according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes,"

and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
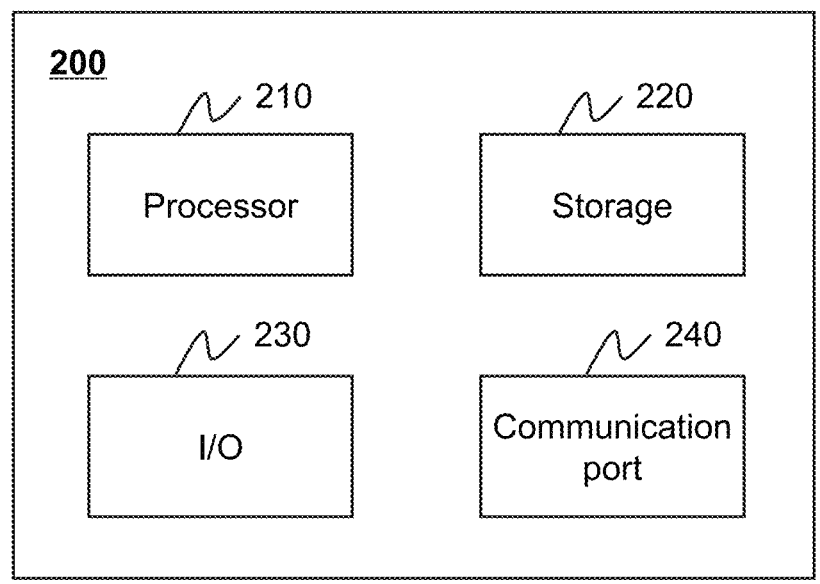
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data) and/or images of various forms, including a two-dimensional (2D) image, a three-dimensional (3D) image, a four-dimensional (4D) image, etc. The term "pixel" and "voxel" in the present disclosure are used interchangeably to refer to an element of an image. The subject may include a biological subject (e.g., a human, an animal), a non-biological subject (e.g., a phantom), etc.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

As used herein, a representation of a subject (e.g., a patient, or a portion thereof) in an image may be referred to as the subject for brevity. For instance, a representation of an organ or tissue (e.g., the heart, the liver, a lung, etc., of a patient) in an image may be referred to as the organ or tissue for brevity. An image including a representation of a subject may be referred to as an image of the subject or an image including the subject for brevity. As used herein, an operation on a representation of a subject in an image may be referred to as an operation on the subject for brevity. For instance, a segmentation of a portion of an image including a representation of an organ or tissue (e.g., the heart, the liver, a lung, etc., of a patient) from the image may be referred to as a segmentation of the organ or tissue for brevity.

An aspect of the present disclosure relates to systems and methods for determining a target scanning phase of an ROI that undergoes a physiological motion. The target scanning phase may be a time point or period in a motion cycle of the ROI that is suitable for scanning the ROI. For example, at the target scanning phase, the ROI may be in a relatively stable motion status. The systems and methods may obtain a reference image (e.g., a positioning image) of the ROI to be scanned by a target scan. The systems and methods may determine a scanning region based on the reference image. The systems and methods may also obtain a plurality of images of the scanning region by performing a pre-scan on the scanning region. The systems and methods may further determine the target scanning phase of the ROI for performing the target scan based on the plurality of images of the scanning region.

Traditionally, before the target scan of the ROI, only a rough range with respect to the target scanning phase is determined, and the target scanning phase (e.g., an optimal phase) is determined after the target scan has been performed on the ROI. For example, the target scanning phase is determined based on the image quality of images corresponding to different phases acquired during the target scan. Generally, the target scan is performed on the ROI based on the rough range of the target scanning phase. The rough range of the target scanning phase is often determined according to physiological motion data of the ROI (e.g., a cardiac motion curve of the heart). For example, for a patient having a relatively high heart rate (e.g., greater than a first heart rate threshold), the systole stage of the patient may be determined as the rough range. As another example, for a patient having a relatively small heart rate (e.g., less than a second heart rate threshold), the diastole phase of the patient may be determined as the rough range.

Since the rough range is determined without considering other individual differences of different ROIs, uncertainty exists in the implementation of the target scan. For example, the rough range may have a limited accuracy, which reduces the scanning effect of the ROI and results in image data with low quality (e.g., with motion artifacts). In some occasions, the rough range is relatively wider than the target scanning phase, resulting in that the ROI receives unnecessary imaging doses during the target scan. Additionally, after the target scan is performed on the ROI, the target scanning phase may need to be determined based on scan data acquired during the target scan, and image reconstruction is performed based on the target scanning phase, which is inefficient (e.g., time-consuming and costs additional computational resources).

According to some embodiments of the present disclosure, before the target scan is performed on the ROI, a pre-san may be performed on a scanning region to obtain a plurality of images. The target scanning phase of the ROI may be determined based on the plurality of images and physiological motion data of the ROI during the pre-scan. In such cases, the target scanning phase can be determined before the target scan is performed. The target scanning phase may be narrower than the rough range, thereby the ROI may receive less imaging dose during the target scan. After the target scan is performed on the ROI under the target scanning phase, the image reconstruction may be performed based on the target scanning phase directly, thereby reducing the time consumed in image reconstruction. In some embodiments, during the determination of the target scanning phase, it may be found that no target scanning phase satisfying a clinical need exists. In other words, it can be known in advance that it is hard to perform the target scan on the ROI successfully, and other solutions need to be adopted (e.g., guidance for adjusting the respiratory motion needs to be provided).

Figure 1:
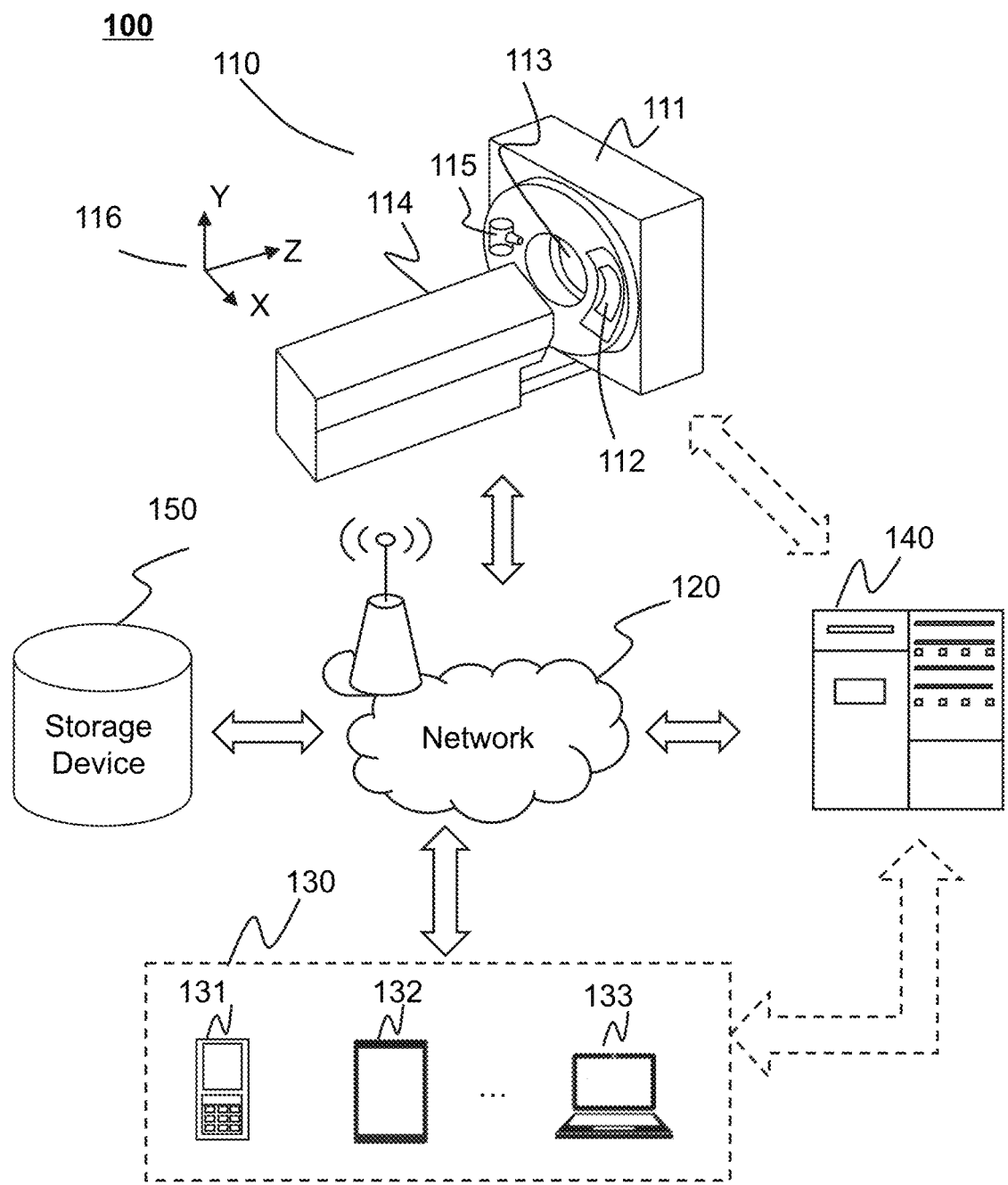
FIG. 1 is a schematic diagram illustrating an exemplary medical imaging system according to some embodiments of the present disclosure.

FIG. 1 is a schematic diagram illustrating an exemplary medical imaging system 100 according to some embodiments of the present disclosure. In some embodiments, the medical imaging system 100 may be used for non-invasive imaging, such as for disease diagnosis, treatment, and/or research purposes. In some embodiments, the medical imaging system 100 may include a single modality system and/or a multi-modality system. The term "modality" used herein broadly refers to an imaging or treatment method or technology that gathers, generates, processes, and/or analyzes imaging information of a subject or treatments the subject. The single modality system may include a computed tomography (CT) system, a digital subtraction angiography (DSA) system, or the like, or any combination thereof. The multi-modality system may include a positron emission tomography-computed tomography (PET-CT) system, a digital subtraction angiography-computed tomography (CT-DSA) system, a computed tomography-magnetic resonance imaging (CT-MRI) system, a digital subtraction angiography-positron emission tomography (DSA-PET) system, a digital subtraction angiography-magnetic resonance imaging (DSA-MRI) system, a computed tomography guided radiotherapy (CT guided RT) system, or the like, or any combination thereof.

As shown in FIG. 1, the medical imaging system 100 may include an imaging device 110, a network 120, a terminal device 130, a processing device 140, and a storage device 150. The components of the medical imaging system 100 may be connected in one or more of various ways. Mere by way of example, as illustrated in FIG. 1, the imaging device 110 may be connected to the processing device 140 through the network 120. As another example, the imaging device 110 may be connected to the processing device 140 directly (as indicated by the bi-directional arrow in dotted lines linking the imaging device 110 and the processing device 140). As a further example, the storage device 150 may be connected to the processing device 140 directly or through the network 120. As still a further example, the terminal device 130 may be connected to the processing device 140 directly (as indicated by the bi-directional arrow in dotted lines linking the terminal device 130 and the processing device 140) or through the network 120.

The imaging device 110 may be configured to scan a subject or a portion thereof. In some embodiments, the subject may include a biological subject (e.g., a patient) or a non-biological subject (e.g., a phantom). For example, the subject may include a specific part, organ, and/or tissue of a patient. As another example, the subject may include the head, the brain, the neck, the breast, the heart, the lung, the stomach, blood vessels, soft tissues, or the like, or any combination thereof. As still another example, the subject may include a region of interest (ROI) that undergoes a physiological motion (e.g., a cardiac motion, a respiratory motion) of a patient. The term "object" or "subject" are used interchangeably in the present disclosure. In some embodiments, the imaging device 110 may include a single modality device. For example, the imaging device 110 may include a CT device, a DSA device, etc. Alternatively, the imaging device 110 may include a multi-modality device (e.g., a double-modality device). For example, the imaging device 110 may include a PET-CT device, a CT-MRI device, a DSA-PET device, a DSA-MRI device, a CT guided RT device, etc. In some embodiments, the imaging device 110 may be part of a treatment device (e.g., a radiotherapy device). For illustration purposes, the imaging device 110 illustrated in FIG. 1 is provided with reference to a CT device, which is not intended to limit the scope of the present disclosure.

As illustrated, the imaging device 110 (e.g., the CT device) may include a gantry 111, a detector 112, a detecting region 113, a table 114, and a radiation source 115. The gantry 111 may support the detector 112 and the radiation source 115. The gantry 111 may rotate, for example, clockwise or counterclockwise about an axis of rotation of the gantry 111. The radiation source 115 and/or the detector 112 may rotate together with the gantry 111. The subject may be placed on the table 114 for scanning. The radiation source 115 may emit a beam of radiation rays to the subject. The detector 112 may detect the radiation beam (e.g., gamma photons) emitted from the radiation source 115. After the detector 112 receives the radiation beam passing through the subject, the received radiation beam may be converted into visible lights. The visible lights may be converted into electrical signals. The electrical signals may be further converted into digital information using an analog-to-digital (AD) converter. The digital information may be transmitted to a computing device (e.g., the processing device 140) for processing, or transmitted to a storage device (e.g., the storage device 150) for storage. In some embodiments, the detector 112 may include one or more detector units. The detector unit(s) may be and/or include single-row detector elements and/or multi-row detector elements.

For illustration purposes, a coordinate system 116 is provided in FIG. 1. The coordinate system 116 may be a Cartesian system including an X-axis, a Y-axis, and a Z-axis. The X-axis and the Z-axis shown in FIG. 1 may be horizontal and the Z-axis may be vertical. As illustrated, the positive X direction along the X-axis may be from the left side to the right side of the table 114 viewed from the direction facing the front of the scanner 110; the positive Z direction along the Z-axis shown in FIG. 1 may be from the end to the head of the table 114; the positive Y direction along the Y-axis shown in FIG. 1 may be from the lower part to the upper part of the imaging device 110.

The processing device 140 may process data and/or information. The data and/or information may be obtained from the imaging device 110, the terminal(s) 130, and/or the storage device 150. For example, the processing device 140 may reconstruct an image of a subject based on scan data obtained from the imaging device 110. As another example, the processing device 140 may determine a target scanning phase for a target scan to be performed on an ROI that undergoes a physiological motion. In some embodiments, the processing device 140 may be a single server or a server group. The server group may be centralized or distributed. In some embodiments, the processing device 140 may be local or remote. For example, the processing device 140 may access information and/or data stored in the imaging device 110, the terminal(s) 130, and/or the storage device 150 via the network 120. As another example, the processing device 140 may be directly connected to the imaging device 110, the terminal(s) 130, and/or the storage device 150 to access stored information and/or data. In some embodiments, the processing device 140 may be implemented on a cloud platform. For example, a cloud platform may include a private cloud, a public cloud, a hybrid cloud, a community cloud, a distributed cloud, an inter-cloud, and a multi-cloud, or the like, or any combination thereof. In some embodiments, the processing device 140 may be implemented by a computing device 200 having one or more components as illustrated in FIG. 2.

The terminal 130 may input/output signals, data, information, etc. In some embodiments, the terminal 130 may enable a user interaction with the processing device 140. For example, the terminal 130 may display an image of the subject on a screen. As another example, the terminal 130 may obtain a user's input information through an input device (e.g., a keyboard, a touch screen, a brain wave monitoring device), and transmit the input information to the processing device 140 for further processing. The terminal 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, a pair of glasses, a helmet, a watch, clothing, a backpack, a smart accessory, or the like, or any combination thereof. In some embodiments, the mobile device may include a mobile phone, a personal digital assistant (PDA), a navigation device, a point of sale (POS) device, a laptop computer, a tablet computer, a desktop computer, or the like, or any combination thereof. In some embodiments, the virtual reality device and/or augmented reality device may include a virtual reality helmet, a pair of virtual reality glasses, a virtual reality patch, an augmented reality helmet, a pair of augmented reality glasses, an augmented reality patch, or the like, or any combination thereof. For example, the virtual reality device and/or augmented reality device may include a Google Glass™, an Oculus Rift™, a HoloLens™, a Gear VR™, or the like. In some embodiments, the terminal 130 may be part of the processing device 140. In some embodiments, the terminal 130 may be integrated with the processing device 140 as an operation station of the imaging device 110. Merely by way of example, a user/operator (for example, a doctor) of the medical imaging system 100 may control an operation of the imaging device 110 through the operation station.

The storage device 150 may store data (e.g., scan data of a subject), instructions, and/or any other information. In some embodiments, the storage device 150 may store data obtained from the imaging device 110, the terminal(s) 130 and/or the processing device 140. For example, the storage device 150 may store scan data of a subject obtained from the imaging device 110. In some embodiments, the storage device 150 may store data and/or instructions executed or used by the processing device 140 to perform exemplary methods described in the present disclosure. In some embodiments, the storage device 150 may include a mass storage device, a removable storage device, a volatile read-write memory, a read-only memory (ROM), or the like, or any combination thereof. For example, the mass storage device may include a magnetic disk, an optical disk, a solid-state drives, a mobile storage, etc. The removable storage device may include a flash drive, a floppy disk, an optical disk, a memory card, a ZIP disk, a magnetic tape, etc. The volatile read-and-write memory may include a random access memory (RAM). The RAM may include a dynamic RAM (DRAM), a double date rate synchronous dynamic RAM (DDR-SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 150 may be implemented by the cloud platform described in the present disclosure. For example, a cloud platform may include a private cloud, a public cloud, a hybrid cloud, a community cloud, a distributed cloud, an inter-clouds, a multi-cloud, or the like, or any combination thereof.

In some embodiments, the storage device 150 may be connected to the network 120 to communicate with one or more components (e.g., the processing device 140, the terminal 130, etc.) of the medical imaging system 100. One or more components of the medical imaging system 100 may access the data or instructions in the storage device 150 via the network 120. In some embodiments, the storage device 150 may be a part of the processing device 140 or may be independent and directly or indirectly connected to the processing device 140.

The network 120 may include any suitable network that can facilitate the exchange of information and/or data of the medical imaging system 100. In some embodiments, one or more components of the medical imaging system 100 (e.g., the imaging device 110, the terminal 130, the processing device 140, the storage device 150, etc.) may communicate information and/or data with one or more components of the medical imaging system 100 via the network 120. The network 120 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, server computers, or the like, or a combination thereof. For example, the network 120 may include a wireline network, an optical fiber network, a telecommunication network, a local area network, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 120 may include one or more network access points. For example, the network 120 may include wired and/or wireless network access points, such as base stations and/or Internet exchange points, through which one or more components of the medical imaging system 100 may be connected to the network 120 to exchange data and/or information.

It should be noted that the above description regarding the medical imaging system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical imaging system 100 may include one or more additional components and/or one or more components of the medical imaging system 100 described above may be omitted. In some embodiments, a component of the medical imaging system 100 may be implemented on two or more sub-components. Two or more components of the medical imaging system 100 may be integrated into a single component.

FIG. 2 is a schematic diagram illustrating exemplary hardware and/or software components of an exemplary computing device according to some embodiments of the present disclosure. The computing device 200 may be configured to implement any component of the medical imaging system 100. For example, the imaging device 110, the terminal 130, the processing device 140, and/or the storage device 150 may be implemented on the computing device 200. Although only one such computing device is shown for convenience, the computer functions relating to the medical imaging system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program codes) and perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal 130 and/or the storage device 150. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal 130, the storage device 150, or any other component of the medical imaging system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, a camera capturing gestures, or the like, or a combination thereof. Exemplary output devices may include a display device, a loudspeaker, a printer, a projector, a 3D hologram, a light, a warning light, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 120) to facilitate data communications. The communication port 240 may establish connections between the processing device 140 and the imaging device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth™ network, a Wi-Fi network, a WiMax network, a WLAN, a ZigBee™ network, a mobile network (e.g., 3G, 4G, 5G), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
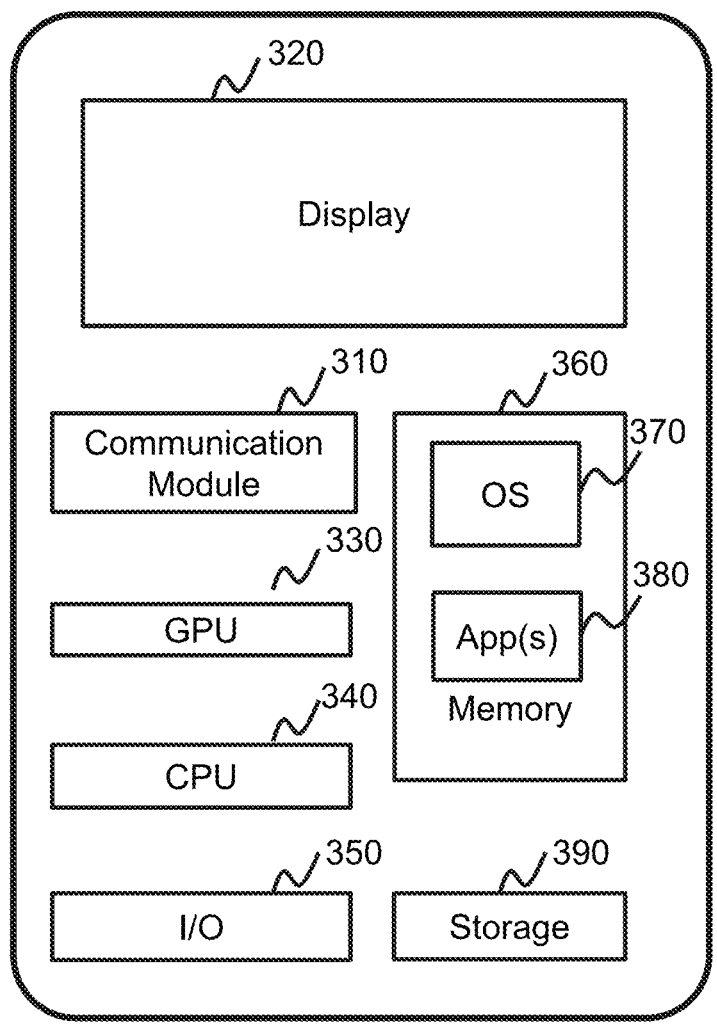
FIG. 3 is a schematic diagram illustrating hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the processing device 140 or the terminal 130 may be implemented on the mobile device 300. As illustrated in FIG. 3, the mobile device 300 may include a communication module 310, a display 320, a graphics processing unit (GPU) 330, a central processing unit (CPU) 340, an I/O 350, a memory 360, and storage 390. The CPU 340 may include interface circuits and processing circuits similar to the processor 210. In some embodiments, any other suitable component, including but not limited to a system bus or a controller (not shown), may also be included in the mobile device 300. In some embodiments, a mobile operating system 370 (e.g., iOS™, Android™ Windows Phone™) and one or more applications 380 may be loaded into the memory 360 from the storage 390 in order to be executed by the CPU 340. The applications 380 may include a browser or any other suitable mobile apps for receiving and rendering information relating to imaging from the blood vessel parameter determination system on the mobile device 300. User interactions with the information stream may be achieved via the I/O devices 350 and provided to the processing device 140 and/or other components of the medical imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
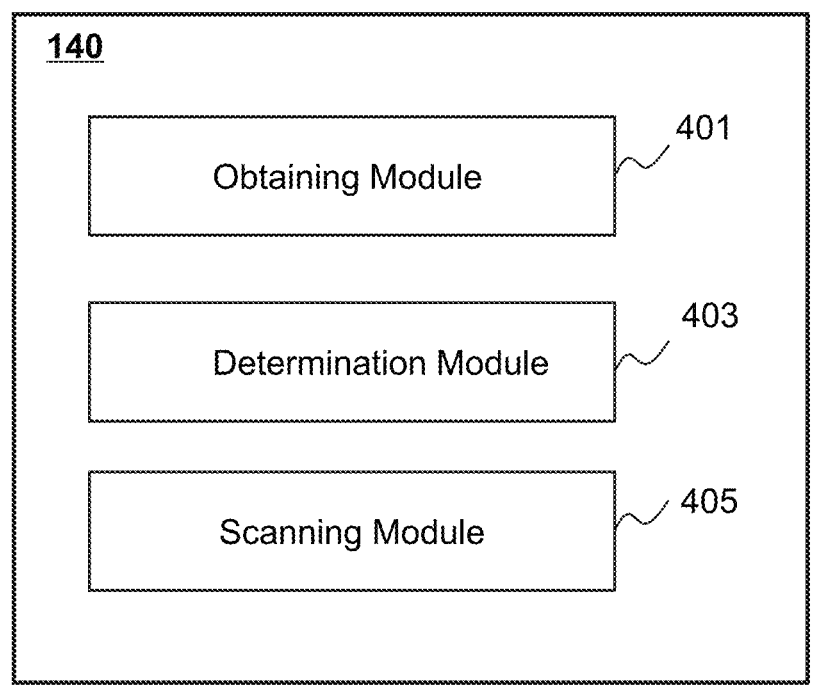
FIG. 4 is a block diagram illustrating an exemplary processing device according to some embodiments of the present disclosure.

FIG. 4 is a schematic diagram illustrating an exemplary processing device according to some embodiments of the present disclosure. As shown in FIG. 4, the processing device 140 may include an obtaining module 401, a determination module 403, and a scanning module 405.

The obtaining module 401 may be configured to obtain data/information relating to the medical imaging system 100. For example, the obtaining module 401 may obtain a reference image of an ROI to be scanned by a target scan, more descriptions of which can be found elsewhere in the present disclosure (e.g., operation 501 and the description thereof). As another example, the obtaining module 401 may obtain a plurality of images of a scanning region of the subject. The plurality of images may be acquired during a pre-scan on the scanning region before a target scan. More descriptions regarding the obtaining of the plurality of images may be found elsewhere in the present disclosure (e.g., operation 505 and relevant descriptions thereof). As still another example, the obtaining module 401 may obtain physiological motion data indicating a physiological motion of the ROI during the pre-scan. For example, the physiological motion data may include a physiological motion curve. More descriptions regarding the obtaining of the physiological motion data may be found elsewhere in the present disclosure (e.g., operation 701 and the description thereof).

The determination module 403 may be configured to determine a target scanning phase of the ROI. For example, for each of the plurality of images, the determination module 403 may determine a feature element from the image. The determination module 403 may determine the target scanning phase of the ROI based on the feature element of each image and the physiological motion data. More descriptions regarding the determination of the target scanning phase may be found elsewhere in the present disclosure (e.g., operation 507, FIG. 7 and relevant descriptions thereof). In some embodiments, the determination module 403 may determine the scanning region based on the reference image of the ROI, description of which can be found elsewhere in the present disclosure (e.g., operation 503 and the description thereof).

The scanning module 405 may be configured to direct an imaging device to perform a scan on the subject or a portion thereof. For example, the scanning module 405 may direct a first imaging device to perform the pre-scan on the scanning region of the subject. The first imaging device may include a CT device, a DSA device, or the like, or any combination thereof. More description regarding the pre-scan may be found elsewhere in the present disclosure (e.g., operation 505, FIG. 11, and relevant descriptions thereof). As another example, the scanning module 405 may direct a second imaging device to perform the target scan on the ROI of the subject according to the target scanning phase of the ROI, description of which can be found elsewhere in the present disclosure (e.g., operation 509 and relevant descriptions thereof).

The modules in the processing device 140 may be connected to or communicated with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth™, a ZigBee™, a Near Field Communication (NFC), or the like, or any combination thereof. Each of the modules described above may be a hardware circuit that is designed to perform certain actions, e.g., according to a set of instructions stored in one or more storage media, and/or any combination of the hardware circuit and the one or more storage media. In some embodiments, the processing device 140 may include one or more other modules and/or one or more modules described above may be omitted. Additionally or alternatively, two or more modules may be integrated into a single module and/or a module may be divided into two or more units. For example, the above-mentioned modules may be integrated into a console (not shown). Via the console, a user may set parameters for scanning a subject, controlling imaging processes, controlling parameters for correcting and/or reconstruction of an image, viewing images, etc. As another example, the processing device 140 may include a storage module (not shown) configured to store information and/or data (e.g., scan data, images) associated with the above-mentioned modules. As still another example, the processing device 140 may include a reconstruction module configured to generate the plurality of images and/or a target image of the ROI.

Figure 5:
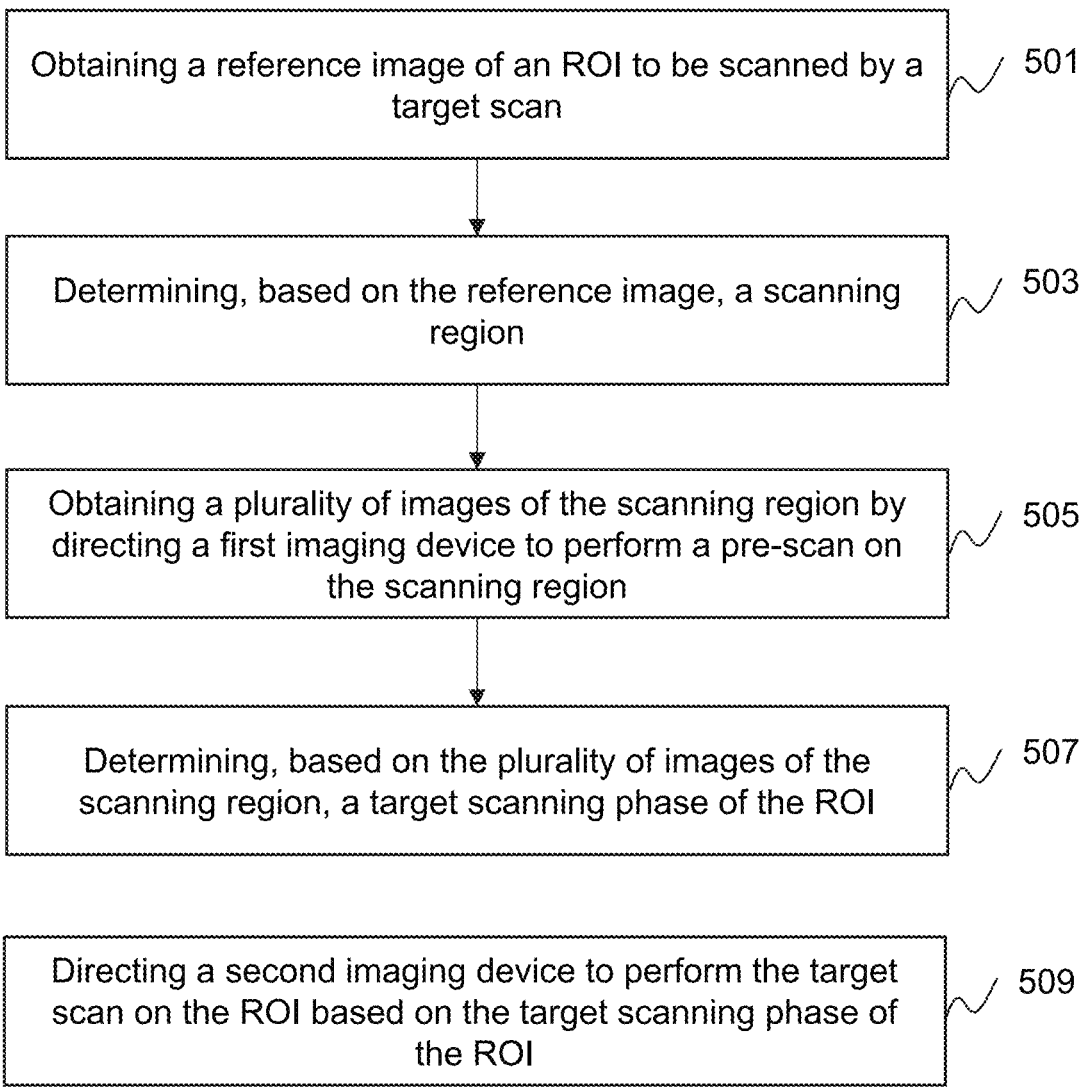
FIG. 5 is a flowchart illustrating an exemplary process for performing a target scanning phase on an ROI according to some embodiments of the present disclosure.

FIG. 5 is a flowchart illustrating an exemplary process for performing a target scan on an ROI according to some embodiments of the present disclosure. In some embodiments, process 500 may be implemented as a set of instructions (e.g., an application) stored in a storage device (e.g., the storage device 130, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 501, the processing device 140 (e.g., the obtaining module 401) may obtain a reference image of the ROI to be scanned by the target scan.

As used herein, the ROI refers to a subject or a specific region of the subject (e.g., a biological subject and/or a non-biological subject) to be scanned by the target scan (e.g., a CT scan, an X-ray scan). The biological subject may be a human being, an animal, or a specific portion thereof (e.g., an organ and/or tissue thereof). For example, the subject may include a patient, and the ROI may include the heart, a lung, etc., of the patient. The non-biological subject may include a phantom of a human being, an animal, or a portion thereof, and the ROI may include the heart, a lung of the phantom. In some embodiments, the ROI may have a physiological motion. For example, the ROI may include the heart of a patient that undergoes a cardiac motion. As another example, the ROI may include the lungs of a patient that undergo a respiratory motion. For illustration purposes, unless otherwise stated, the following descriptions are provided with reference to an ROI including the heart of a patient. It is understood that this is for illustration purposes and not intended to be limiting. The systems and methods disclosed herein may be applied to image other types of ROIs.

The reference image may include anatomical information of the ROI. In some embodiments, the reference image may be a 2-dimensional image of the ROI. In some embodiments, the reference image of the ROI may include a positioning image of the ROI that can be used to obtain position information of different portions of the ROI. For example, the reference image of the ROI may include a topo image of the ROI including a sagittal image, a coronary image, or an axial image of the ROI. In some embodiments, the reference image may be previously generated and stored in a storage device (e.g., the storage device 150, the storage 220, or the storage 390) of the medical imaging system 100 or an external storage device (e.g., a medical image database). The processing device 140 may retrieve the reference image from the storage device or the external storage device.

For example, historical positioning images of different reference subjects and information of each reference subject may be stored in the storage device. Information of each reference subject may include, such as a height, a weight, an ROI to be scanned by a historical target scan, etc. of the reference subject. The processing device 140 may determine the reference image from the historical positioning images by matching information of the subject with the information of the reference subjects. For instance, the processing device 140 may determine, among the reference subjects, a specific reference subject whose information has the highest similar degree to that of the subject. The processing device 140 may determine the reference image of the ROI based on a historical positioning image of the specific reference subject, e.g., by designating the historical positioning image of the specific reference subject as the reference image of the ROI.

In some embodiments, the reference image may be generated in real-time. For example, the processing device 140 may direct the medical device 110 (e.g., a CT device, a DSA device, an X-ray device, a CT-DSA device, an X-ray-DSA device, etc.) to perform an initial scan on the ROI at a certain angle. The processing device 140 may generate the reference image of the ROI based on scan data acquired during the initial scan. As another example, the processing device 140 may direct the medical device 110 to scan the ROI under multiple scanning angles. The processing device 140 may generate multiple positioning images (e.g., a sagittal image, a coronary image, and/or an axial image) of the ROI based on scan data acquired under the multiple scanning angles. By using the multiple positioning images, the scanning region described in 503 may be determined more accurately.

In 503, the processing device 140 (e.g., the determination module 403) may determine, based on the reference image, a scanning region.

As used herein, the scanning region refers to a region of the subject on which a pre-scan is performed. The "determining the scanning region" may be also referred to as determining a portion in the reference image that corresponds to the scanning region. In some embodiments, the scanning region may include a portion of the ROI that has relatively large motion amplitude. For example, the scanning region may include a region of the ROI that has a motion amplitude larger than a preset threshold in a motion cycle of the ROI. For instance, the scanning region may include at least a portion of a middle region of the ROI along the z-axis (e.g., the middle of the heart that has a relatively larger cardiac motion than the apex and the base of the heart). Because the scanning region is relatively smaller than the original ROI, the ROI may receive a relatively smaller imaging dose (e.g., the radiation dose) during the pre-scan. In some embodiments, since a physiological motion of the ROI can be reflected by a motion of the boundary of the ROI, the scanning region may include at least a portion of a boundary of the ROI. In some embodiments, the scanning region may also include a portion of the subject that is adjacent to the ROI. For example, if the ROI is the heart of a patient, the scanning region may include the middle of the heart and a portion of the lungs near the middle of the heart.

Figure 6A:
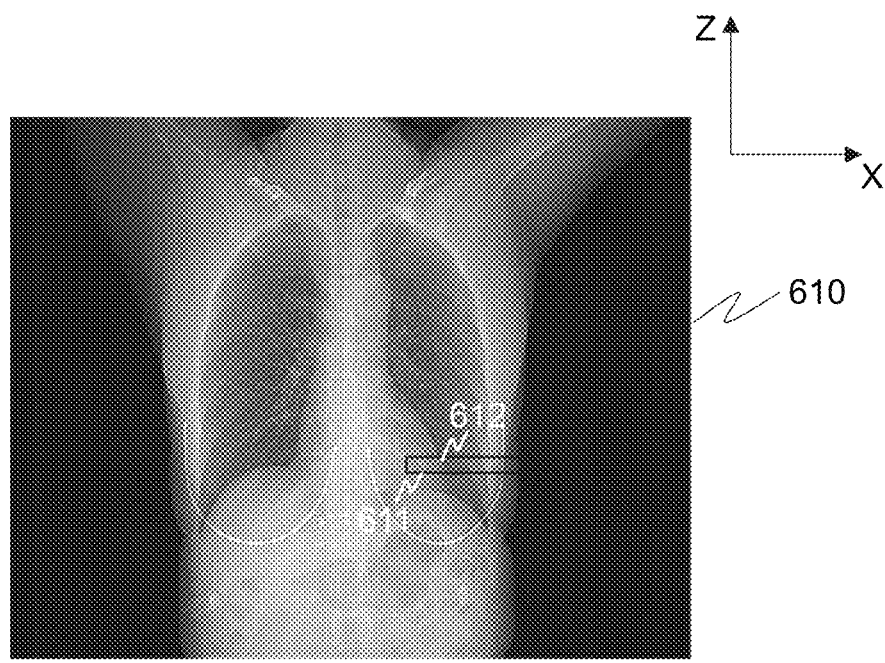
FIG. 6A and FIG. 6B are schematic diagram illustrating exemplary scanning regions of an ROI according to some embodiments of the present disclosure.
Figure 6B:
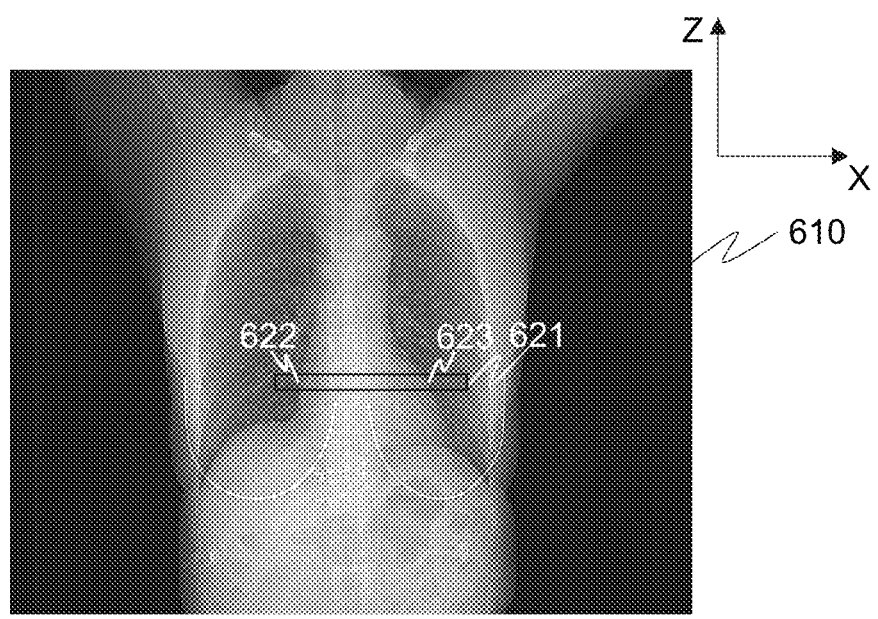

In some embodiments, the processing device 140 may determine the scanning region based on a goal of the target scan. For example, the goal of the target scan may include examining a specific part of the ROI (e.g., a left coronary artery of the heart). As shown in FIGS. 6A and 6B, a reference image 610 of the heart of a patient is a coronary positioning image of the heart of the patient acquired by a CT device. As shown in FIG. 6A, if the target scan is used to examine the left coronary artery of the heart, a scanning region 611, which includes a left portion of the middle region of the heart and a portion of the left lung of the patient close to the left portion of the middle region of the heart, is determined. The scanning region 611 may include a segment 612 of the boundary of the heart. The scanning region 611 may be used to determine a target scanning phase of the left coronary artery of the heart. In some embodiments, the scanning region 611 may correspond to one or more lines of image elements (e.g., pixels) of the reference image 611. For example, the scanning region 611 may correspond to one line of pixels in the reference image 611 such that the region of the patient to be scanned in the pre-scan may be as small as possible.

As shown in FIG. 6B, if the target scan is used to examine the whole heart, a scanning region 621, which includes the middle region of the heart, a portion of the left lung of the patient close to the left portion of the middle region of the heart, and a portion of the right lung of the patient close to the right portion of the middle region of the heart, is determined. The scanning region 612 may include two segments (e.g., a segment 622 and a segment 623) of the boundary of the heart. The scanning region 621 may be used to determine a target scanning phase of the heart. In some embodiments, the scanning region 621 may be used to determine a target scanning phase of the left coronary artery of the heart and a target scanning phase of the right coronary artery of the heart.

In some embodiments, the processing device 140 may determine the scanning region based on a user instruction indicating a location and a size of a portion that represents the scanning region in the reference image. For example, the processing device 140 may receive a user instruction input by a user (e.g., an operator or a doctor) of the medical imaging system 100, e.g., according to a user experience and the reference image. The processing device 140 may determine the scanning region based on the user instruction. In some embodiments, the processing device 140 may obtain profile information of the subject (e.g., an age of a patient, a gender of the patient, or a specific part of the patient to be scanned by the target scan, etc.). The processing device 140 may determine the scanning region based on the profile information and the reference image automatically.

In 505, the processing device 140 (e.g., the obtaining module 401, and the scanning module 405) may obtain a plurality of images by performing the pre-scan on the scanning region (e.g., by directing a first imaging device to perform the pre-scan on the scanning region).

In some embodiments, the processing device 140 may direct the first imaging device (e.g., a CT device or a DSA device) to perform the pre-scan on the scanning region, and generate the images based on data acquired in the pre-scan. In some embodiments, the images may be sequentially acquired with the subject being located at a fixed position relative to a radiation source of the first imaging device. For example, a gantry and a table of the first imaging device may be in a static state during the pre-scan. A collimation width of the first imaging device may be consistent with a width of the scanning region along the z-axis. In such cases, the scanning angle of the scanning region during the pre-scan may remain constant. It should be understood that the scanning region may move due to the physiological motion of the ROI during the pre-scan, and when the position of the subject relative to the radiation source remains unchanged in the pre-scan, an actual region being scanned may change in the pre-scan. For example, in the pre-scan on the scanning region, the actual region being scanned may include only a portion of the scanning region and/or additional regions near the scanning region due to the physiological motion of the ROI.

In some embodiments, the processing device 140 may direct the radiation source of the first imaging device to keep emitting radiation rays and a detector of the first imaging device to acquire a plurality of sets of scan data of the scanning region at a plurality of acquisition times during the pre-scan. Alternatively, the processing device 140 may direct the radiation source of the first imaging device to emit radiation rays at the plurality of acquisition times during the pre-scan. The plurality of acquisition times may have a fixed time interval or a varied time interval between each pair of adjacent acquisition times of the acquisition times. In some embodiments, the ROI may undergo at least one motion cycle during the pre-scan. A time length of the pre-scan may be equal to a time length of the at least one motion cycle. Taking the heart of the patient as an example, a time length of the at least one motion cycle may be 1 second ~ 2 seconds. The time interval between each pair of adjacent acquisition times may be equal to 100 us. The processing device 140 may direct the detector of the first imaging device to acquire a set of scan data of the scanning region of the heart every 100 us.

In some embodiments, the subject may be injected with a contrast agent before the pre-scan, which can enhance the display of the ROI in the plurality of images of the scanning region (e.g., enhance a projection of the coronary artery of the heart) and improve the accuracy of the plurality of images obtained by the pre-scan, thereby improving the accuracy of the target scanning phase determined in subsequent operations. The contrast agent injected to the subject may have a relatively small dose, e.g., less than a dose threshold or as long as the display of the ROI can be enhanced, which is not limited herein. For example, before the pre-scan, the processing device 140 may send a notification to instruct a user of the medical imaging system 100 to inject the contrast agent into the subject. After the subject is injected with the contrast agent, the processing device 140 may direct the first imaging device to perform the pre-scan on the scanning region.

Further, the processing device 140 may generate the plurality of images based on the sets of scan data of the scanning region acquired at the plurality of acquisition times during the pre-scan. Accordingly, the plurality of images may be regarded as an image sequence including images corresponding to the acquisition times. The plurality of images may correspond to the same scanning angle. In some embodiments, the scanning angle may be a default setting of the medical imaging system 100 (e.g., a zero angle) or be determined by the user of the medical system 100. Alternatively, the scanning angle may be determined automatically, details of which may be found elsewhere in the present disclosure (e.g., FIG. 11 and the relevant description thereof). In some embodiments, the plurality of images may be previously generated and stored in a storage device (e.g., a storage device of the medical imaging system 100 or an external storage device), and the processing device 140 may obtain the images from the storage device.

In 507, the processing device 140 (e.g., the determination module 403) may determine, based on the plurality of images of the scanning region, a target scanning phase of the ROI.

As used herein, a target scanning phase of the ROI refers to a target time point or a target time period when the ROI is in a target motion status in a motion cycle of the ROI. Taking the heart as an exemplary ROI, the target scanning phase of the heart may correspond to a target time point at which or a target time period during which the heart is in a steady status or a static status. If the motion amplitude of the heart at a specific time point is the smallest among all time points over the motion cycle of the heart, the heart may be deemed as being in a steady status at the target time point, and the target time point may be deemed as the target scanning phase. As another example, if a variation of the motion amplitude of the heart during a specific time period in the motion cycle is relatively small (e.g., a difference between the largest motion amplitude and the smallest motion amplitude of the heart in the specific time period being less than a difference threshold), the heart may be deemed as being in a steady status at the target time period, and the target time period may be deemed as the target scanning phase.

In some embodiments, the processing device 140 may obtain physiological motion data (e.g., a physiological motion curve) indicating a physiological motion of the ROI during the pre-scan. The processing device 140 may further determine an initial range (e.g., an initial time interval) based on the physiological motion data. For each of the plurality of images, the processing device 140 may determine a feature element from the image. The processing device 140 may determine the target scanning phase of the ROI based on the initial range and the feature element of each image.

In some embodiments, the scanning region may include multiple sub-regions. The processing device 140 may determine a target scanning phase for each of the multiple sub-regions based on the plurality of images of the scanning region. The multiple sub-regions may correspond to multiple portions of the ROI, and a target scanning phase for a specific sub-region may be regarded as a target scanning phase of the ROI that corresponds to the specific sub-region. For example, the heart of the patient may include the left coronary artery and the right coronary artery having different motion features. It is possible that the left coronary artery and the right coronary have different target scanning phases. Merely by way of example, the scanning region 621 of the heart as shown in FIG. 6B may include a first sub-region corresponding to the left coronary artery and a second sub-region corresponding to the right coronary artery. The processing device 140 may determine a first feature element from the first sub-region in each of the images and a second feature element from the second sub-region in each of the images. The processing device 140 may further determine a first target scanning phase for the left coronary artery based on the first feature elements, and a second target scanning phase for the right coronary artery based on the second feature elements. The first and second target scanning phases may be used in image reconstruction for the left coronary artery and the right coronary artery, respectively. More descriptions regarding the determination of the target scanning phase based on the physiological motion data and the plurality of images may be found elsewhere in the present disclosure (e.g., FIGS. 7 and 8 and the descriptions thereof).

In 509, the processing device 140 (e.g., the scanning module 405) may direct a second imaging device to perform the target scan on the ROI based on the target scanning phase of the ROI.

In some embodiments, if the target scanning phase is a target time point in a motion cycle of the ROI, the processing device 140 may determine a target time period based on the target time point. For example, the target time point may be a mid-point of the target time period. The processing device 140 may direct the second imaging device (e.g., a CT device) to perform the target scan on the ROI according to the target time period. During the target scan, data acquisition may only be performed during the target time period. If the target scanning phase is the target time period in a motion cycle of the ROI, the processing device 140 may directly direct the second imaging device to perform the target scan on the ROI according to the target time period. In some embodiments, the ROI may undergo multiple motion cycles during the target scan. During the target scan, data acquisition may be performed during the target time period in each of the multiple motion cycles. For the convenience of descriptions, scan data collected during the target time period in the target scan is referred to as target scan data.

For example, the second imaging device may include a CT device. During the target scan, the processing device 140 may direct a radiation source (e.g., a radiation tube) of the CT device to emit radiation rays (e.g., X-rays) during the target time period and be in a closed state or a stand-by state at other time. Alternatively, the processing device 140 may direct the radiation source of the CT device to keep emitting radiation rays during the target scan, and adjust a position of a collimator relative to the radiation source based on the target scanning phase. For instance, during the target time period, the processing device 140 may direct the collimator to be at a first position relative to the radiation source such that radiation rays may pass through a light field formed by the collimator to irradiate the ROI; and at other time, the processing device 140 may direct the collimator to be at a second position relative to the radiation source such that radiation rays may be blocked by the collimator and prevented from irradiating the ROI. In some embodiments, in the premise of ensuring the imaging effect, the ROI may be irradiated by radiation rays only during the target time period, thereby reducing unnecessary radiations received by the ROI. In some embodiments, during the target scan, the radiation source of the CT device may rotate around the ROI in an angle range. Optionally, the span of the angle range may exceed a threshold angle so that enough target scan data of the ROI can be collected. For example, the threshold angle may be 180°, 200° 240°, etc.

As another example, the second imaging device may include an MRI device. The processing device 140 may direct the MRI device to perform an MRI scan (i.e., the target scan) on the ROI based on the target scanning phase. For example, the processing device 140 may direct the MRI device to apply an MRI pulse sequence (e.g., by driving a radiofrequency (RF) coil of the MRI device to transmit an RF pulse, driving a gradient coil of the MRI device to generate a gradient pulse, etc.) during the target time period. The processing device 140 may direct the RF coil of the MRI device to be detuned and/or a gradient amplifier to stop driving the gradient coil at other time. In such cases, the RF pulse absorbed by the ROI may be reduced, an electromagnetic radiation energy absorbed by the subject including the ROI per unit mass of matter per unit time may be reduced, a specific absorption rate of sensitive portion(s) of the subject may below a threshold, and a switching frequency of a gradient field generated by the gradient coil may be reduced to reduce the peripheral nervous system (PNS) effect.

After the target scan data is acquired, the processing device 140 may generate a target image of the ROI based on the target scan data using a reconstruction algorithm. For example, an MRI image of the ROI may be reconstructed based on MRI data collected during the target time period according to an MRI reconstruction algorithm. As another example, a CT image of the ROI may be reconstructed based on CT data collected during the target time period according to a CT reconstruction algorithm, such as a filtered-back projection (FBP) algorithm, an iterative reconstruction (IR) algorithm, a reconstruction algorithm using a machine learning model, etc.

In some embodiments, for the CT device, the processing device 140 may generate the target image of the ROI based on the target scanning phase and the target scan data of the ROI acquired during the target scan. For example, when the target scanning phase is a target time point, the processing device 140 may determine a target acquisition angle corresponding to the target time point (e.g., a scanning angle of the radiation source when the subject is at the target time point). The processing device 140 may obtain a target angle range centred at the target acquisition angle. That is, a middle acquisition angle of the target angle range may be the target acquisition angle. A width of the target angle range may be, for example, 180°, 200°, 240° etc. Merely by way of example, assuming that the target acquisition angle is 90° and the width of the target angle range is 180°, the target angle range may be 0°-180°. The processing device 140 may determine a portion of target scan data acquired within the target angle range, and generate the target image based on the determined portion.

In some embodiments, as aforementioned, multiple target scanning phases corresponding to multiple sub-regions of the ROI may be determined. In such cases, the processing device 140 may direct the second imaging device to perform the target scan on the ROI according to the multiple target scanning phases. For example, a target time period corresponding to each of the multiple target scanning phases may be determined, and data acquisition may be performed within the target time periods during the target scan. Further, for each of the multiple target scanning phases, the processing device 140 may generate a target image of the ROI based on target scan data of the ROI acquired during a target time period corresponding to the target scanning phase.

In some embodiments, in a target image corresponding to a specific target scanning phase, different portions of the ROI may have different image qualities. For instance, in the target image, a portion of the ROI corresponding to the specific target scanning phase may have a higher image quality than other portions of the ROI. For example, as described in connection with operation 507, the processing device 140 may determine a first target scanning phase corresponding to the left coronary artery and a second target scanning phase corresponding to the right coronary artery. The processing device 140 may generate a first target image of the heart based on the first target scanning phase. In the first target image, the left coronary artery of the heart may have a higher resolution than the right coronary artery of the heart. The processing device 140 may also generate a second target image of the heart of the patient based on the second target scanning phase. In the second target image, the right coronary artery of the heart may have a higher resolution than the left coronary artery of the heart. In some embodiments, both the first and second target images may be displayed to a user (e.g., a doctor), so that the user can diagnose both the left coronary artery and the right coronary artery of the heart. In this way, different portions of the ROI having different motion characteristics can be analysed and examined separately, which improves the examination accuracy.

In some embodiments, the processing device 140 may direct the second imaging device to perform the target scan on the ROI, and data acquisition may be performed during the whole target scan. After the target scan, the processing device 140 may generate the target image of the subject based on target scan data acquired during the target time period corresponding to the target scanning phase of the ROI. Merely by way of example, the second imaging device may include a PET device. The processing device 140 may direct the PET device to perform a PET scan (i.e., the target scan) on the ROI. In the image reconstruction process, the processing device 140 may utilize target scan data acquired during the target time period during the PET scan, and scan data acquired at other times during the PET scan may not be used. This may reduce or eliminate the effect of the physiological motion (e.g., a cardiac motion, a respiratory motion, etc.) of the ROI on the reconstructed PET image of the ROI and improve the quality of the PET image, e.g., the PET image may include less motion artifact.

In some embodiments, the second imaging device for performing the target scan and the first imaging device for performing the pre-scan may be of a same type as or different types. For example, the first and second imaging devices may be a same CT device. As another example, the first imaging device may include a CT device or a DSA device, while the second imaging device may include an MRI device, a PET device, etc.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more additional operations may be added in the process 500. For example, a storing operation may be added elsewhere in the process 500. In the storing operation, the processing device 140 may store information and/or data used or obtained in operations of the process 500 in a storage device (e.g., the storage device 150) disclosed elsewhere in the present disclosure. In some embodiments, one or more operations of the process 500 may be omitted. For example, operations 501 and 503 may be integrated to be performed by a single operation.

Figure 7:
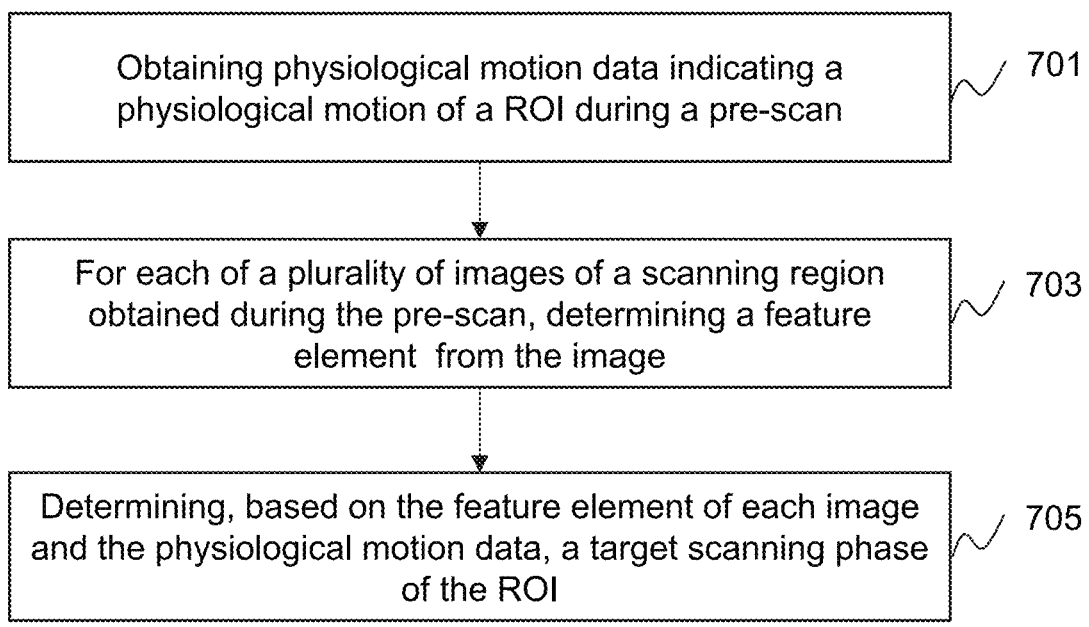
FIG. 7 is a flowchart illustrating an exemplary process for determining a target scanning phase of an ROI according to some embodiments of the present disclosure.

FIG. 7 is a flowchart illustrating an exemplary process for determining a target scanning phase of an ROI according to some embodiments of the present disclosure. In some embodiments, process 700 may be implemented as a set of instructions (e.g., an application) stored in a storage device (e.g., the storage device 130, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, at least part of operation 507 in FIG. 5 may be achieved by the process 700.

In 701, the processing device 140 (e.g., the obtaining module 401) may obtain physiological motion data indicating a physiological motion of the ROI during the pre-scan.

In some embodiments, the physiological motion data may include a physiological motion curve indicating a variation of a motion amplitude of the ROI over time during the pre-scan. For example, the physiological motion curve may include a respiratory motion curve, a cardiac motion curve, a pulse curve, etc. The physiological motion curve may reflect motion cycle(s) of the ROI during the pre-scan and/or different stages of the ROI in each of the motion cycle(s) during the pre-scan. Taking the cardiac motion curve as an example, the cardiac motion curve may reflect motion amplitudes of the cardiac motion of the heart at different time points during the pre-scan. For example, the cardiac motion curve may reflect motion cycle(s) of the heart during the pre-scan. As another example, the cardiac motion curve may reflect different stages of the heart in each of the motion cycle(s) during the pre-scan. The different stages of the heart may include a systole stage, a diastole stage, etc. Each of the different stages may correspond to a time period (or time interval) of the motion cycle.

In some embodiments, the physiological motion data may be collected during the pre-scan by a physiological motion detection device. Exemplary physiological motion detection devices may include an electrocardiograph (ECG) monitor, a respiratory monitor, a pulse monitor, or the like. In some embodiments, the physiological motion detection device may be integrated into a smart device (e.g., a wearable device) worn by the subject including the ROI. The processing device 140 may obtain the physiological motion data from the physiological motion detection device or a storage device that stores the physiological motion data. For example, a cardiac motion curve of the heart of the patient may be detected by an ECG monitor during the pre-scan of the patient, and the processing device 140 may obtain the cardiac motion curve from the ECG monitor.

In 703, for each of the plurality of images of the scanning region obtained during the pre-scan, the processing device 140 (e.g., the determination module 403) may determine a feature element from the image.

For illustration purposes, it is assumed that the pre-scan is a CT scan, and the images are 2D CT images of the scanning region. Each of the plurality of images may include a plurality of pixels (also referred to as elements). A pixel of each image of the plurality of images may correspond to a plurality of physical points (or voxels) of the scanning region. For example, during the pre-scan, a radiation ray emitted from a radiation source of the first imaging device may pass through a set of physical points and an energy of the radiation ray may attenuate. The attenuated radiation ray may be detected by a detector unit of the first imaging device, and the detector unit may collect projection data (e.g., a projection value) corresponding to the set of physical points. The projection data corresponding to the set of physical points may be used to determine a pixel value of a pixel representing the sets of physical points in an image.

In some embodiments, the plurality of images may correspond to a same image coordinate system. For illustration purposes, it is assumed that a central axis of the radiation source of the first imaging device is parallel to the Y-axis of the coordinate system 116 as shown in FIG. 1, and the image coordinate system may be parallel to the X-Z plane of the coordinate system 116, thus a coordinate of a pixel in an image may be denoted by an X-coordinate and a Z-coordinate.

A feature element of an image refers to a specific pixel determined from a plurality of pixels of the image. In some embodiments, the processing device 140 may determine, based on at least one of the plurality of images, a target coordinate. Further, for each of the plurality of images, the processing device 140 may determine, from the image, an element having the target coordinate as the feature element of the image. A pixel having the target coordinate in each image may represent a feature physical point or a physical point near the feature physical point of the ROI. A feature physical point of the ROI may move due to the physiological motion of the ROI. For example, the feature physical point of the ROI may be a boundary point of the ROI, and a pixel in an image having the target coordinate corresponding to the boundary point may represent the boundary point or a physical point near the boundary point (e.g., a physical point located within a certain distance away from the boundary point).

For example, in any one of the plurality of images and/or the reference image, the processing device 140 may identify a pixel corresponding to a feature physical point on the boundary of the ROI. The processing device 140 may determine a coordinate of the identified pixel as the target coordinate, and determine a pixel having the target coordinate from each of the images as a feature element. Accordingly, a pixel having the target coordinate in each image, which is likely to represent a boundary point of the ROI, may be determined as a feature element for subsequent analysis.

As another example, for each at least two of the plurality of images (e.g., two images acquired at two adjacent acquisition times in a motion cycle of the ROI), the processing device 140 may determine a projection value curve corresponding to the image. The projection value curve of an image may include projection values of the pixels in the image (or a portion thereof). The processing device 140 may determine the target coordinate based on the projection value curves corresponding to the at least two of the images. In some embodiments, each image may include one or more lines of pixels, wherein pixels of a same line may have different X-coordinates and the same Z-coordinate. For example, each image may include only one line of pixels corresponding to a specific Z-coordinate. As another example, each image may include two lines of pixels. One line of pixels may correspond to a first Z-coordinate and the other line of pixels may correspond to a second Z-coordinate. In some embodiments, the processing device 140 may determine a specific line from the one or more lines of pixels for subsequent analysis. For example, projection values of pixels in the specific line may have a greater fluctuation over time than projection values of pixels in each of the other line(s). For each of the at least two of the images, the processing device 140 may generate a projection value curve of the pixels in the specific line of the image.

Figure 9:
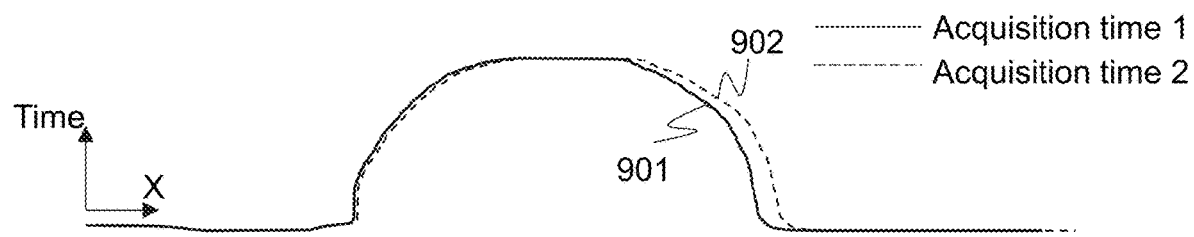
FIG. 9 is a schematic diagram illustrating exemplary projection value curves of two images acquired at two acquisition times respectively according to some embodiments of the present disclosure.

For instance, as shown in FIG. 9, a projection value curve 901 of a first image acquired at an acquisition time 1 and a projection value curve 902 of a second image acquired at an acquisition time 2) are generated. The projection value curve 901 indicates projection values of a line of first pixels in the first image, the projection value curve 902 indicates projection values of a line of second pixels in the second image, and the first and second pixels have the same Z-coordinate. A horizontal direction in FIG. 9 denotes X-coordinates of the first and second pixels, and a vertical direction in FIG. 9 denotes projection values of the first and second pixels. For each X-coordinate of the first and second pixels, the processing device 140 may determine a difference between projection values of a first pixel and a second pixel having the X-coordinate. The processing device 140 may determine an X-coordinate corresponding to a maximum difference among the differences. The processing device 140 may further designate the determined X-coordinate and the Z-coordinate of the first and second pixels as the target coordinate. In other words, the projection values of pixels having the target coordinate in the images may have a greater variation over time more than other pixels, which indicates that these pixels may provide more information about the physiological motion of the ROI and can be designated as feature elements of the images.

In some embodiments, for each of the plurality of images, the processing device 140 may determine a target projection value based on the image, and determine an element having the target projection value as the feature element of the image. Similarly to the target coordinate, a pixel having the target projection value in each image may represent a feature physical point or a physical point near the feature physical point of the ROI. For example, for an image, the processing device 140 may determine a plurality of projection values of a plurality of elements in the image. The processing device 140 may determine, among the plurality of projection values, a maximum projection value. The processing device 140 may determine the target projection value based on the maximum projection value, e.g., the target projection value may be equal to a half of the maximum projection value. Since the plurality of images correspond to substantially the same scanning region, maximum projection values in the plurality of images may be equal or close in size. Accordingly, the feature elements of the plurality of images may have an equal projection value or close projection values. As another example, the target projection value of an image may be a default setting of the medical imaging system 100 or can be adjustable by the processing device 140 according to different situations. As yet another example, the processing device 140 may determine the target projection value according to a user's instruction.

In 705, the processing device 140 (e.g., the determination module 403) may determine, based on the feature element of each image and the physiological motion data, the target scanning phase of the ROI.

In some embodiments, the processing device 140 may determine, based on the physiological motion data, an initial time interval during which the ROI is in a steady status (e.g., a variation of the motion amplitude of the ROI being less than a variation threshold). For example, for a patient having a relatively high heart rate (e.g., greater than a heart rate threshold), the processing device 140 may determine the systole stage of the heart of the patient based on the cardiac motion data of the heart. The processing device 140 may determine a time interval corresponding to the systole stage as the initial time interval of the heart. As another example, for a patient having a relatively small heart rate (e.g., less than a heart rate threshold), the processing device 140 may determine the diastole stage of the heart of the patient based on the cardiac motion data of the heart. The processing device 140 may determine a time interval corresponding to the diastole stage as the initial time interval of the heart.

In some embodiments, as aforementioned, the feature element of each image may correspond to a same target coordinate. In such cases, for each of the plurality of images, the processing device 140 may determine a projection value of the feature element of the image. The processing device 140 may determine a first variation of the projection values of the feature elements of the plurality of images over time. The processing device 140 may determine, from the initial time interval, the target scanning phase based on the first variation. For example, the first variation may be denoted by a first variation curve, wherein a horizontal direction and a vertical direction may represent the time and the projection value, respectively. If the target scanning phase is a target time point, the processing device 140 may determine a specific time point within the initial time interval as the target scanning phase. A derivative of the first variation curve may be minimum at the specific time point within the initial time interval. For example, the minimum derivative may be 0. If the target scanning phase is a target time period, the processing device may determine a specific time period within the initial time interval as the target scanning phase. A derivative of the first variation curve may be below a first derivative threshold at each time point in the specific time period within the initial time interval.

In some embodiments, as aforementioned, the feature element of each image may correspond to a target projection value of the image. In such cases, for each of the plurality of images, the processing device 140 may determine a coordinate (e.g., an X-coordinate) of the feature element of the image. The processing device 140 may determine a second variation of the coordinates of the feature elements of the plurality of images over time. The processing device 140 may determine, from the initial time interval, the target scanning phase based on the second variation. For example, the second variation may be denoted by a second variation curve, wherein a horizontal direction and a vertical direction represent the time and the coordinate, respectively. If the target scanning phase corresponds to a target time point, the processing device 140 may determine a specific time point within the initial time interval as the target scanning phase. A derivative of the second variation curve may be minimum at the specific time point within the initial time interval. For example, the minimum derivative may be 0. If the target scanning phase is a target time period, the processing device may determine a specific time period within the initial time interval as the target scanning phase. A derivative of the second variation curve may be below a second derivative threshold at each time point in the specific time period within the initial time interval.

Figure 10:
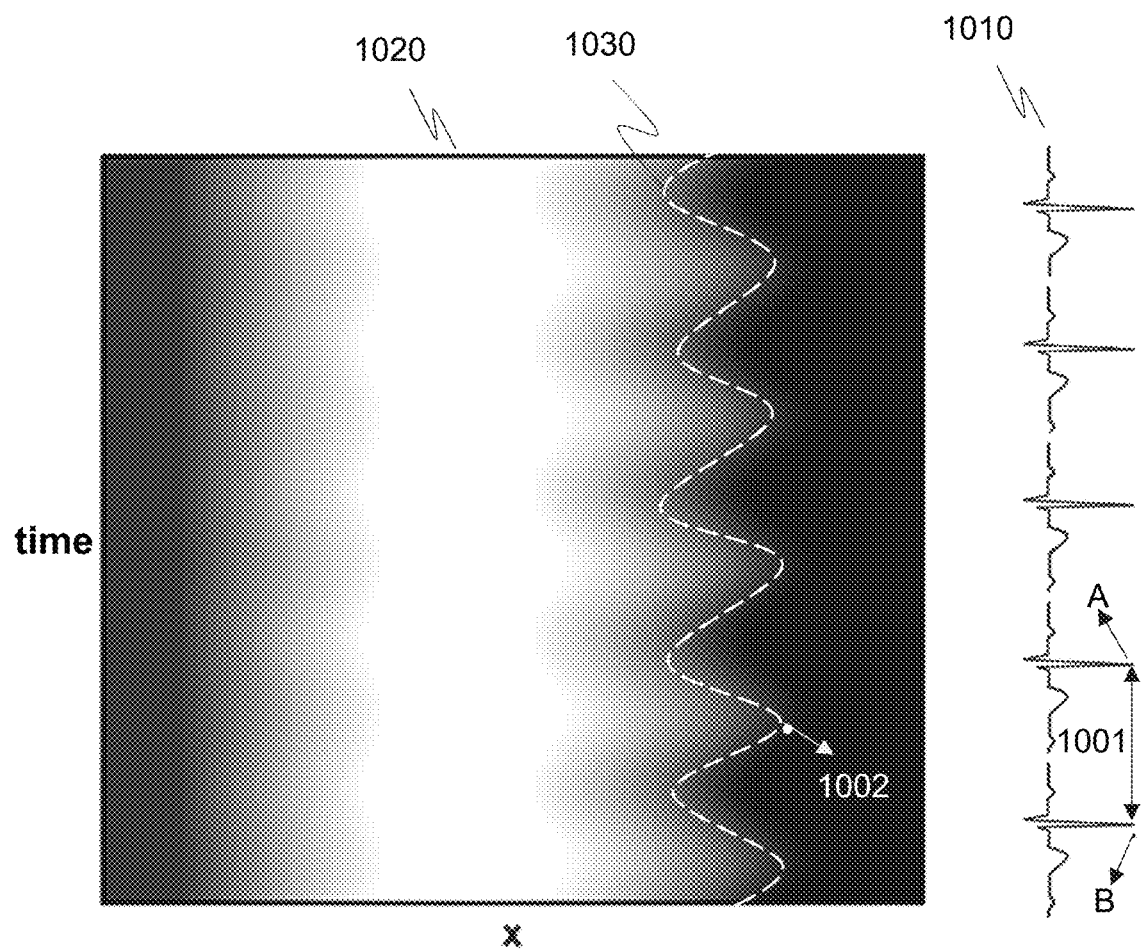
FIG. 10 is a schematic diagram illustrating an exemplary projection value graph for determining a target scanning phase according to some embodiments of the present disclosure according to some embodiments of the present disclosure.

For illustration purposes, FIG. 10 illustrates an exemplary projection value graph for determining a target scanning phase according to some embodiments of the present disclosure. As shown in FIG. 10, a cardiac motion curve 1010 was acquired during a pre-scan of a scanning region. According to the cardiac motion curve 1010, the pre-scan was performed during more than four cardiac motion cycles 1001 of the heart of a patient. A projection value graph 1020 illustrates three-dimensional information of the heart of a patient during the pre-scan. A horizontal direction of the projection value graph 1020 denotes X-coordinates of pixels of a line in each of a plurality of images acquired during the pre-scan, a vertical direction of the projection value graph 1020 denotes the time, and the brightness of a point in the projection value graph 1020 indicates a projection value of a corresponding pixel. For example, a specific point having a horizontal coordinate of x and a vertical coordinate of t in the projection value graph 1020 may correspond to a pixel having the X-coordinate of x in an image acquired at the acquisition time t during the pre-scan. The lighter the specific point is, the greater the projection value of the corresponding specific pixel may be. A second variation curve 1030 in FIG. 10 illustrates a second variation of the coordinates of the feature elements of the plurality of images over time. Based on the second variation curve 1030 and the cardiac motion curve 1010, a point 1002, which corresponds to a specific time point within an initial time interval of the cardiac motion cycle 1010, is determined from the second variation curve 1030. The point 1002 may be at a valley position of the second variation curve 1030 at which a derivative of the second variation curve 1030 is minimum. The specific time point corresponding to the point 1002 may be denoted as the target scanning phase of the heart of the patient for performing a target scan on the heart of the patient.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more additional operations may be added in the process 700. For example, a storing operation may be added elsewhere in the process 700. In the storing operation, the processing device 140 may store information and/or data used or obtained in operations of the process 700 in a storage device (e.g., the storage device 150) disclosed elsewhere in the present disclosure. In some embodiments, an operation of the process 700 may be achieved by two or more sub-operations. For example, the operation 703 may be achieved by two sub-operations. One sub-operation may be performed to determine the initial time interval based on the physiological motion data, and another sub-operation may be performed to determine the target scanning phase based on the feature element of each image and the initial time interval.

In some embodiments, for each of the plurality of images, the processing device 140 may determine more than one feature element (e.g., multiple feature elements) for subsequent analysis. Merely by way of example, the multiple feature elements in the image may be located at a same line and correspond to different sub-regions of the ROI. For example, the multiple feature elements in the image may include a first feature element corresponding a first sub-region of the ROI and a second feature element corresponding to the second sub-region of the ROI. The processing device 140 may determine a first target scanning phase corresponding to the first sub-region of the ROI based on the first feature elements in the plurality of images. The processing device 140 may determine a second target scanning phase corresponding to the second sub-region of the ROI based on the second feature elements in the plurality of images.

In some embodiments, an image may include one or more lines of pixels. For each of the plurality of images, the processing device 140 may determine more than one line of pixels for subsequent analysis. For instance, a first line and a second line may be used to determine the target scanning phase. For each of the plurality of images, the processing device 140 may determine a first feature element in the first line and a second feature element in the second line. The processing device 140 may determine a first scanning phase based on the first feature elements in the plurality of images. The processing device 140 may determine a second scanning phase based on the second feature elements in the plurality of images. The processing device 140 may determine the target scanning phase based on the first scanning phase and the second scanning phase (e.g., by averaging the first scanning phase and the second scanning phase).

In some embodiments, the processing device 140 may determine the target scanning phase based on pixel values instead of projection values. For example, the target scanning phase may be determined based on a third variation of the pixel values of the feature elements of the plurality of images over time. The determination of the target scanning phase based on the third variation may be performed in a similar manner as that based on the first variation as aforementioned. As another example, for each of the plurality of images, the processing device 140 may determine a target pixel value based on the image, and determine an element having the target pixel value as the feature element of the image for subsequent analysis. The determination of the target pixel value of each image may be performed in a similar manner as that of the target projection value of each image as aforementioned.

In some embodiments, the processing device 140 may determine the target scanning phase based on the image sequence (i.e., the plurality of images acquired during the pre-scan) and ECG signals of the subject. For example, the processing device 140 may determine a time interval in the image sequence corresponding to ECG signals with calm variation as the target scanning phase. It should be noted that ECG signals corresponding to the physiological motion curve may be synchronized with ECG signals corresponding to the image sequence.

In some embodiments, the processing device 140 may determine a scanning region based on a positioning image of the subject. The processing device 140 may obtain an image sequence by performing a pre-scan on the scanning region. The processing device 140 may determine a target scanning phase based on the image sequence and an ECG curve of the subject. Because the target scanning phase is determined based on the image sequence of the subject and the ECG curve of the subject, and the image sequence of the subject and the ECG curve of the subject can reflect the motion of the heart of the subject accurately, the target scanning phase may be accurately determined. In addition, the target scanning phase may be determined before the target scan, such that the processing device 140 can direct the second imaging device to perform the target scan on the subject according to the target scanning phase, thereby improving the accuracy of the target scan.

In some embodiments, to determine the target scanning phase based on the image sequence and the physiological motion curve of the subject, the processing device 140 may determine a variation of projection values of each physical point (or referred to as a voxel) in the scanning region over time. The variation of the projection values of each physical point may be consistent with a motion value of the physical point. The processing device 140 may determine a variation of projection values of one or more physical points of interest (POIs) over time based on the variation of projection values of each physical point in the scanning region over time. The processing device 140 may determine the target scanning phase based on the variation of projection values of each POI over time and the physiological motion curve. If the physiological motion curve is a cardiac motion curve (e.g., an ECG curve) or a pulse curve, the POI may include a cardiac physical point (e.g., a physical point of the heart of the subject). If the physiological motion curve is a respiratory motion curve, the POI may include a lung physical point (e.g., a physical point of a lung of the subject).

In the above-described scenario that the processing device 140 determines the target scanning phase according to the image sequence and the ECG curve of the subject, the processing device 140 may determine projection values of each cardiac physical point of the subject at different time points based on the image sequence, and determine the target scanning phase based on the projection values of each cardiac physical point of the subject at different time points, more descriptions of which may be found in the elsewhere of the present disclosure (e.g., FIG. 8 and the description thereof).

FIG. 8 is a flowchart illustrating an exemplary process for determining a target scanning phase of a target object according to some embodiments of the present disclosure. In some embodiments, process 800 may be implemented as a set of instructions (e.g., an application) stored in a storage device (e.g., the storage device 130, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting. In some embodiments, operation 507 in FIG. 5 may be achieved by the process 800.

In 801, the processing device 140 (e.g., the determination module 403) may determine a variation of projection values of each physical point in the scanning region over time based on an image sequence of the scanning region.

In some embodiments, for each image of the image sequence, the processing device 140 may determine a projection value of each pixel of a plurality of pixels in the image. The processing device 140 may determine a variation of projection values of each physical point in the scanning region over time based on the projection value of each pixel in each image. For example, projection values at different positions of the heart of a subject are shown in FIG. 9. As shown in FIG. 9, the solid line 901 is a first projection value curve of pixels corresponding to a same Z-coordinate in the scanning region at a first time point (i.e., the acquisition time 1). For example, the Z-axis may be parallel to a long axis direction of the body of the subject. The dotted line 902 is a second projection value curve of the pixels corresponding to the same Z-coordinate in the scanning region at a second time point (i.e., the acquisition time 2). In FIG. 9, a horizontal axis represents different physical points that have the same Z-coordinate in the scanning region, and a vertical axis reflects projection values of the physical points or motion values of the physical points. It should be noted that because of the motion of the heart, the projection value of the heart of the subject at each position would vary over time. For a stationary physical point, a projection value corresponding to the stationary physical point in the first projection value curve may be equal or substantially equal to a projection value corresponding to the stationary physical point in the second projection curve (e.g., projection values corresponding to the stationary physical point are equal at different time points). For a moving physical point, a projection value of the moving physical point in the first projection value curve may vary with a projection value of the moving physical point in the second projection curve (e.g., projection values corresponding to some sets of physical points may be different at different time points). For example, the variation of the projection values may be reflected by a deviation of the first projection value curve from the second projection value curve at different time points.

In 803, the processing device 140 (e.g., the determination module 403) may determine a variation of projection values of each POI over time based on the variation of projection values of each physical point in the scanning region over time. For example, a POI may include a physical point of the heart (or a cardiac physical point).

In some embodiments, FIG. 10 illustrates a schematic diagram illustrating projection values of each physical point in the image sequence of the scanning region. As shown in FIG. 10, the horizontal axis denotes coordinates along the left-right direction of the subject under a coronary position, and the vertical axis denotes the time. Different grayscales indicate projection values of different POIs. In FIG. 10, a region in which projection values are homogenized may correspond to stationary physical points, and a boundary region of two different grayscales may correspond to moving physical points or POIs (e.g., the projection value of a moving physical point may have a periodical change). For example, the POIs may include cardiac physical points. The processing device 140 may determine the variation of projection values of each physical point in the scanning region over time, and determine the variation of projection values of each POI over time. It should be appreciated that the projection values at different positions of the heart of the subject may be used to determine the boundary of the heart of the subject. The outline of the heart may change with the motion of the heart. For example, the boundary of the heart may be determined based on projection values of the heart at different positions as indicated by the solid line 901 to the dotted line 902 as shown in FIG. 9. For instance, the processing device 140 may detect the projection values at different positions of the heart using a boundary detection algorithm. The processing device 140 may determine a boundary at each position of the heart at each time point to determine a boundary value at each position of the heart at each time point. The processing device 140 may determine a motion value of the heart of the subject based on the boundary value at each position of the heart at each time point.

In 805, the processing device 140 (e.g., the determination module 403) may determine the target scanning phase based on the variation of projection values of each POIs over time and a physiological motion curve (e.g., an ECG curve).

In some embodiments, the processing device 140 may determine a target time interval (i.e., the initial time interval) based on the physiological motion curve, e.g., a time interval during which the heartbeat is relatively calm. The processing device 140 may determine, from the target time interval, a time interval during which a variation of projection values of each POI is less than a preset threshold as the target scanning phase. That is, the processing device 140 may determine a time interval within the target time interval, during which a variation of projection values of each POI is the minimum, as the target scanning phase.

In some embodiments, when the processing device 140 determines the target time interval based on the physiological motion curve, the processing device 140 may detect projection values at different positions (e.g., different time points) of the physiological motion curve using a boundary detection algorithm to determine a boundary value of the physiological motion curve at each time point. The processing device 140 may determine the target time interval based on the boundary value of the physiological motion curve at each time point. For example, the processing device 140 may determine a time interval during which the boundary value of the physiological at each time point is minimum as the target time interval. For the POI being the cardiac POI, the physiological motion curve may include an ECG curve.

In some embodiments, as shown in FIG. 10, in the image 1020, grayscales periodically change, which indicates that projection values of the POIs (e.g., cardiac physical points) change over time. The right part of FIG. 10 illustrates an ECG (motion) curve 1010 acquired using an ECG monitor or a navigation sequence. A motion cycle (e.g., the motion cycle 1001) of the heart may be between two adjacent peaks (e.g., peaks A and B) of the ECG curve 1010. The processing device 140 may determine a phase (e.g., a time point) in a motion cycle of the heart, which corresponds to a valley value of a change rate of projection values of a POI over time, as the target scanning phase.

In some embodiments, the processing device 140 may determine a variation of projection values of each physical point in a scanning region over time based on the image sequence, such that the processing device 140 may determine a variation of projection values of each cardiac physical point over time based on the variation of projection values of each physical points in a scanning region over time accurately. In this way, the processing device 140 may determine a target scanning phase based on the variation of projection values of each cardiac physical point over time accurately, thereby improving the accuracy of the determined target scanning phase.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 11:
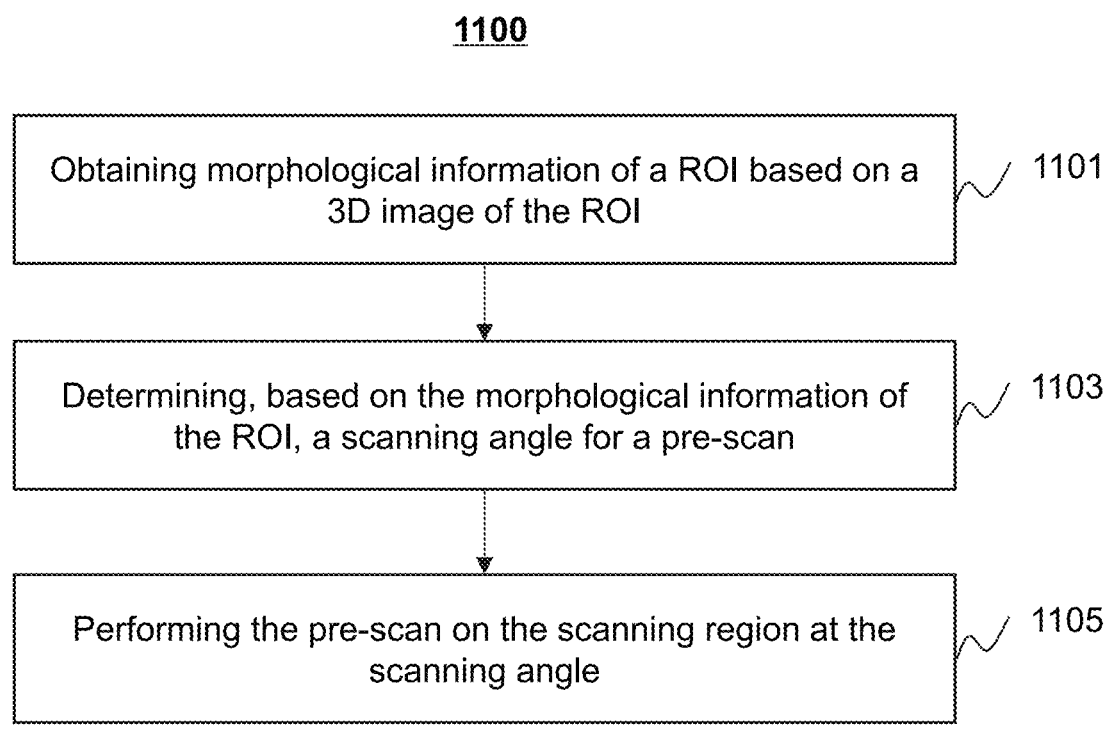
FIG. 11 is a flowchart illustrating an exemplary process for performing a pre-scan on an ROI according to some embodiments of the present disclosure.

FIG. 11 is a flowchart illustrating an exemplary process for performing a pre-scan on a scanning region according to some embodiments of the present disclosure. In some embodiments, process 1100 may be implemented as a set of instructions (e.g., an application) stored in a storage device (e.g., the storage device 130, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 1100. The operations of the illustrated process presented below are intended to be illustrative. In some embodiments, the process 1100 may be accomplished with one or more additional operations not described and/or without one or more of the operations discussed. Additionally, the order of the operations of process 1100 illustrated in FIG. 11 and described below is not intended to be limiting. In some embodiments, at least a portion of operation 505 may be achieved by the process 1100.

In 1101, the processing device 140 (e.g., the scanning module 405) may obtain morphological information of the ROI based on a 3D image of the ROI.

The morphological information may include shape information, size information, contour information, position information (e.g., a position of the ROI with respect to the subject including the ROI or the first imaging device that performs the pre-scan), etc., or any combination thereof, of the ROI. In some embodiments, the 3D image of the ROI may include a calcium scoring image of the ROI. The calcium scoring image of the ROI refers an image that can reflect a calcium condition of the ROI. For example, before the pre-scan is performed, the processing device 140 may direct the first imaging device or the second imaging device to perform an initial scan on the ROI to obtain the calcium scoring image of the ROI. As another example, the calcium scoring image of the ROI may be pre-stored in a storage device of the medical imaging system 100. The processing device 140 may retrieve the calcium scoring image of the ROI from the storage device.

In some embodiments, the processing device 130 may segment the 3D image (e.g., the calcium scoring image) of the ROI according to a segmentation algorithm. Exemplary segmentation algorithms may include a threshold-based segmentation algorithm (e.g., an Otsu segmentation algorithm, a GrowCUT segmentation algorithm, etc.). The processing device 140 may determine the morphological information of the ROI based on the segmentation result. For example, the morphological information of the heart of a patient may include a position of an aortic annulus plane, an aortic sinus plane with the maximum diameter, a sinus tube junction plane, an ascending aorta plane, a coronary artery opening plane, a left ventricular outflow tract plane, etc., of the heart of the patient. In some embodiments, the cardiac motion of the heart of the patient is generated from the beat of the atriums and/or the ventricles of the heart. The processing device 140 may determine a position of the atrial(s) and/or the ventricular(s) based on the calcium scoring image of the heart, and designate the determined position as the morphological information of the heart or part of the morphological information.

In 1103, the processing device 140 (e.g., the scanning module 405) may determine, based on the morphological information of the ROI, a scanning angle for the pre-scan.

For example, if the first imaging device is an X-ray imaging device (e.g., a CT device), a scanning angle may be defined by an angle between a central axis of the radiation source of the first imaging device and a reference direction (e.g., the X-axis direction or the Y-axis direction). In some embodiments, for the heart of the patient, an idle scanning angle may be perpendicular to a beat direction of the atriums and/or the ventricles of the heart. For example, the central axis of the radiation source of the first imaging device may be set to be perpendicular to the beat direction of the atriums and/or the ventricles of the heart. It can be understood that the beat of atriums and/or the ventricles of the heart may be similar to a periodically expanding sphere, the surface of the sphere may protrude outwards along an expansion direction when the sphere expands, and a tangent direction of the surface of the sphere at the expansion direction may be perpendicular to the expansion direction. The beat direction may be similar to the expansion direction, and the central axis of the radiation source of the pre-scan to be set may be similar to the tangent direction.

In some embodiments, since the surface of the atriums and/or the ventricles is covered by a coronary artery of the heart and a position of the coronary artery relative to the atriums and/or the ventricles is relatively fixed, the processing device 140 may determine a specific branch of the coronary artery of the heart for determining the scanning angle for the pre-scan. For example, if a goal of the target scan is to scan a left coronary artery of the heart, the processing device 140 may determine a position of the left coronary artery of the heart based on the morphological information of the ROI. The processing device 140 may determine a position of a branch of the left coronary artery that covers the left atrium and/or the left ventricle of the heart. The processing device 140 may determine the scanning angle based on the position of the branch of the left coronary artery and the position of the branch of the left coronary artery relative to the left atrium and/or the left ventricle of the heart. As another example, the processing device 140 may determine a centerline of the specific branch of the coronary artery of the heart. The processing device 140A may determine a tangent direction of the specific branch based on the centerline of the specific branch of the coronary artery. The processing device 140A may determine a direction perpendicular to the tangent direction as the beat direction. The processing device 1340A may determine the scanning angle for the pre-scan based on the beat direction.

In 1105, the processing device 140 (e.g., the scanning module 405) may perform the pre-scan on the scanning region at the scanning angle.

In some embodiments, during the pre-scan, the radiation source of the first imaging device may be fixed at a specific position and emit radiation rays towards the scanning region from the scanning angle to obtain the plurality of images of the scanning region. That is, the subject may be located at a fixed position relative to the radiation source of the first imaging device. More descriptions regarding the pre-scan may be found elsewhere in the present disclosure (e.g., operation 505 and the description thereof).

In some embodiments, the processing device 140 may direct the first imaging device to perform a plurality of pre-scans on the scanning region at multiple scanning angles. The processing device 140 may determine a plurality of images acquired at an optimal scanning angle of the multiple scanning angles for determining the target scanning phase of the ROI. The pre-scan at the optimal scanning angle may better reflect the physiological motion of the ROI than the pre-scan(s) at other scanning angle(s). For example, the multiple pre-scans may include a first pre-scan, a second pre-scan, etc. The first pre-scan (e.g., an anteroposterior scan) may be performed at a first scanning angle to obtain a plurality of first images. The second pre-scan (e.g., a lateral scan) may be performed at a second scanning angle to obtain a plurality of second images. The processing device 140 may determine the plurality of first images or the plurality of second images for determining the target scanning phase of the ROI, e.g., by evaluating the motion amplitudes of the ROI reflected by the first images and the second images.

According to some embodiments of the present disclosure, the processing device 140 may determine the scanning angle based on the morphological information of the ROI and perform the pre-scan on the scanning region at the scanning angle, which can take individual differences of different subjects into consideration. In this way, the pre-scan can be performed on the scanning region more accurately and the plurality of images acquired during the pre-scan may be more accurate.

In some embodiments, considering that the ROIs of different subjects are located at different positions, operations 1101 and 1103 may be applied to determine a scanning angle at which the reference image (e.g., a positioning image) is obtained. For example, if the ROI is the heart of the patient, the processing device 140 may obtain morphological information of the heart based on a calcium scoring image of the heart. The processing device 140 may determine an optimal scanning angle based on the morphological information of the heart, and the optimal scanning angle may be used to obtain a positioning image of the heart. Accordingly, the accuracy of the positioning image may be improved, e.g., by avoiding other regions (e.g., a spine, a rib, etc.) of the patient from covering the heart of the patient in the positioning image.

It should be noted that the above description regarding the process 1100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more additional operations may be added in the process 1100. For example, a storing operation may be added elsewhere in the process 1100. In the storing operation, the processing device 140 may store information and/or data used or obtained in operations of the process 1100 in a storage device (e.g., the storage device 150) disclosed elsewhere in the present disclosure. In some embodiments, one or more operations of the process 1100 may be achieved by an operation. For example, the operations 1101 and 1103 may be achieved by a single operation.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
    at least one storage device including a set of instructions for scanning a region of interest (ROI) of a subject, the ROI undergoing a physiological motion; and
    at least one processor configured to communicate with the at least one storage device, wherein when executing the set of instructions, the at least one processor is configured to direct the system to perform operations including:
        obtaining a reference image of the ROI to be scanned by a target scan;
        determining, based on the reference image, a scanning region;
        obtaining a plurality of images of the scanning region by performing a pre-scan on the scanning region; and
        determining, based on the plurality of images of the scanning region, a target scanning phase of the ROI for performing the target scan by:
            obtaining physiological motion data indicating the physiological motion of the ROI during the pre-scan;
            for each of the plurality of images, determining a feature element from the image; and
            determining, based on the feature element of each image and the physiological motion data, the target scanning phase of the ROI.

2. The system of claim 1, wherein the plurality of images are sequentially acquired during the pre-scan with the subject being located at a fixed position relative to a radiation source of an imaging device.

3. The system of claim 1, wherein the determining, based on the feature element of each image and the physiological motion data, the target scanning phase of the ROI includes:
    determining, based on the physiological motion data, an initial time interval during which the ROI is in a steady status; and
    determining, from the initial time interval, the target scanning phase of the ROI based on the feature element of each image.

4. The system of claim 3, wherein for each of the plurality of images, the determining a feature element from the image includes:
    determining, based on at least one of the plurality of images, a target coordinate; and
    for each of the plurality of images, determining, from the image, an element having the target coordinate as the feature element of the image.

5. The system of claim 4, wherein the determining, from the initial time interval, the target scanning phase of the ROI based on the feature element of each image includes:
    for each of the plurality of images, determining a projection value of the feature element of the image;
    determining a first variation of the projection values of the feature elements of the plurality of images over time; and
    determining, from the initial time interval, the target scanning phase based on the first variation.

6. The system of claim 3, wherein for each of the plurality of images, the determining a feature element from the image includes:
    for each of the plurality of images,
        determining, based on the image, a target projection value; and
        determining, from the image, an element having the target projection value as the feature element of the image.

7. The system of claim 6, wherein the determining, based on the image, a target projection value corresponding to a feature point of the ROI includes:
    determining a plurality of projection values of a plurality of elements in the image;
    determining, among the plurality of projection values, a maximum projection value; and determining the target projection value based on the maximum projection value.

8. The system of claim 6, wherein the determining, from the initial time interval, the target scanning phase of the ROI based on the feature element of each image includes:
for each of the plurality of images, determining a coordinate of the feature element of the image;
determining a second variation of the coordinates of the feature elements of the plurality of images over time; and
determining, from the initial time interval, the target scanning phase based on the second variation.

9. The system of claim 1, wherein the physiological motion data includes an electrocardiograph (ECG) curve.

10. The system of claim 1, wherein
the ROI includes the heart of a subject, and the physiological motion includes a cardiac motion; or
the ROI includes the lungs of a subject, and the physiological motion includes a respiratory motion.

11. The system of claim 1, wherein the subject is injected with a contrast agent before the pre-scan.

12. The system of claim 1, wherein the scanning region includes multiple sub-regions, and the determining, based on the plurality of images of the scanning region, a target scanning phase of the ROI for performing the target scan further includes:
determining, based on the plurality of images of the scanning region, a target scanning phase for each of the multiple sub-regions, and wherein the operations further include:
directing an imaging device to perform the target scan on the ROI according to the target scanning phases corresponding to the multiple sub-regions; and
for each of the multiple target scanning phases, generating a target image of the ROI based on target scan data of the ROI acquired during a target time period corresponding to the target scanning phase.

13. The system of claim 1, wherein the performing the pre-scan on the scanning region includes:
obtaining morphological information of the ROI based on a 3D image of the ROI;
determining, based on the morphological information of the ROI, a scanning angle for the pre-scan; and
performing the pre-scan on the scanning region at the scanning angle.

14. A method implemented by a computing device including at least one processor and at least one storage device, comprising:
obtaining a reference image of the ROI to be scanned by a target scan;
determining, based on the reference image, a scanning region;
obtaining a plurality of images of the scanning region by performing a pre-scan on the scanning region; and
determining, based on the plurality of images of the scanning region, a target scanning phase of the ROI for performing the target scan by:
obtaining physiological motion data indicating the physiological motion of the ROI during the pre-scan;
for each of the plurality of images, determining a feature element from the image; and
determining, based on the feature element of each image and the physiological motion data, the target scanning phase of the ROI.

15. The method of claim 14, wherein the plurality of images are sequentially acquired during the pre-scan with the subject being located at a fixed position relative to a radiation source of an imaging device.

16. The method of claim 14, wherein the determining, based on the feature element of each image and the physiological motion data, the target scanning phase of the ROI includes:
determining, based on the physiological motion data, an initial time interval during which the ROI is in a steady status; and
determining, from the initial time interval, the target scanning phase of the ROI based on the feature element of each image.

17. The method of claim 14, wherein the physiological motion data includes an electrocardiograph (ECG) curve.

18. A non-transitory computer readable medium, comprising executable instructions that, when executed by at least one processor, direct the at least one processor to perform a method for scanning a region of interest (ROI) of a subject, the ROI undergoing a physiological motion, the method comprising:
obtaining a reference image of the ROI to be scanned by a target scan;
determining, based on the reference image, a scanning region;
obtaining a plurality of images of the scanning region by performing a pre-scan on the scanning region; and
determining, based on the plurality of images of the scanning region, a target scanning phase of the ROI for performing the target scan by:
obtaining physiological motion data indicating the physiological motion of the ROI during the pre-scan;
for each of the plurality of images, determining a feature element from the image; and
determining, based on the feature element of each image and the physiological motion data, the target scanning phase of the ROI.

19. The system of claim 1, wherein the physiological motion data includes a physiological motion curve indicating a variation of a motion amplitude of the ROI over time during the pre-scan.

20. The method of claim 14, wherein the physiological motion data includes a physiological motion curve indicating a variation of a motion amplitude of the ROI over time during the pre-scan.

* * * * *